(12) United States Patent
Okumura et al.

(10) Patent No.: US 9,730,883 B2
(45) Date of Patent: Aug. 15, 2017

(54) PROPHYLACTIC OR THERAPEUTIC AGENT FOR ORAL DISEASES

(75) Inventors: Takekazu Okumura, Tachikawa (JP); Tomohiko Terai, Kawasaki (JP); Masumi Nakao, Hachioji (JP); Kimiyuki Kaneko, Fuchu (JP); Masahiko Ito, Kokubunji (JP); Kouji Miyazaki, Fuchu (JP); Kazuaki Yamaji, Mitaka (JP); Kaoru Tochiya, Kawasaki (JP); Nobuhiro Hanada, Yokohama (JP); Susumu Imai, Higashimurayama (JP); Yoshiaki Nomura, Adachi-ku (JP); Shunsuke Baba, Kyoto (JP)

(73) Assignee: KABUSHIKI KAISHA YAKULT HONSHA, Tokyo (JP)

( * ) Notice: Subject to any disclaimer, the term of this patent is extended or adjusted under 35 U.S.C. 154(b) by 156 days.

(21) Appl. No.: 14/236,849

(22) PCT Filed: Aug. 3, 2012

(86) PCT No.: PCT/JP2012/069916
§ 371 (c)(1),
(2), (4) Date: Feb. 3, 2014

(87) PCT Pub. No.: WO2013/021957
PCT Pub. Date: Feb. 14, 2013

(65) Prior Publication Data
US 2014/0178313 A1 Jun. 26, 2014

(30) Foreign Application Priority Data
Aug. 5, 2011 (JP) ................... 2011-171891

(51) Int. Cl.
*A61K 39/07* (2006.01)
*A61K 8/99* (2017.01)
*C12R 1/225* (2006.01)
*C12R 1/46* (2006.01)
*C12N 1/20* (2006.01)
*A61K 35/744* (2015.01)
*A61K 35/747* (2015.01)
*A61Q 11/00* (2006.01)
*C12Q 1/68* (2006.01)
*A23L 2/52* (2006.01)
*A61K 9/20* (2006.01)
*A23L 29/00* (2016.01)
*A23L 33/135* (2016.01)

(52) U.S. Cl.
CPC *A61K 8/99* (2013.01); *A23L 2/52* (2013.01); *A23L 29/065* (2016.08); *A23L 33/135* (2016.08); *A61K 9/2018* (2013.01); *A61K 35/744* (2013.01); *A61K 35/747* (2013.01); *A61Q 11/00* (2013.01); *C12N 1/20* (2013.01); *C12Q 1/68* (2013.01); *C12R 1/225* (2013.01); *C12R 1/46* (2013.01)

(58) Field of Classification Search
None
See application file for complete search history.

(56) References Cited

U.S. PATENT DOCUMENTS

| 6,036,952 | A | 3/2000 | Oh |
| 2002/0094328 | A1 | 7/2002 | De Simone |
| 2007/0071737 | A1 | 3/2007 | Koga |

FOREIGN PATENT DOCUMENTS

| JP | 2001 512670 | 8/2001 |
| JP | 2003 502375 | 1/2003 |
| JP | 4203855 | 1/2009 |
| WO | WO 99/07826 A1 | 2/1999 |
| WO | WO 00/78322 A2 | 12/2000 |

OTHER PUBLICATIONS

Gibbons, et al. "Model Delineating the Effects of a Salivary Pellicle on the Adsorption of *Streptococcus miteor* onto Hydroxyapatite" (Infection and Immunity: Oct. 1976: vol. 14: p. 1109-1112).
Busscher, et al. "In vitro Adhesion to Enamel and in vivo Colonization of Tooth Surfaces by Lactobacilli from a Bio-Yoghurt" (Caries Research: 1999: vol. 33: p. 403-404).
Extended European Search Report issued on Jan. 29, 2015 in European Patent Application No. 12822146.2.
Kanari, Y. et al., "A Review of Intervention Studies for Prevention of Falls in Older People", Jpn J Public Health, vol. 49, pp. 287-304, (2002) (with English abstract and partial English translation).
"Research Report on Business for Improving Elderly people's Health-care and Health, Survey Report on the Support Systems for the Oral care in the Elderly Health-care Facility and Special Elderly Nursing Home", Institute for Health Economics and Policy, Annual Report of Investigation and Researches, Total 165 Pages, (Mar. 1996) (with partial English translation).

(Continued)

*Primary Examiner* — Ja'na Hines
*Assistant Examiner* — Khatol Shahnan Shah
(74) *Attorney, Agent, or Firm* — Oblon, McClelland, Maier & Neustadt, L.L.P.

(57) ABSTRACT

Provided is a novel lactic acid bacterium strain which is capable of suppressing production of volatile sulfur compounds by oral bacteria, has no cariogenicity and no causative role in infective endocarditis, and is safe in an oral cavity, and provided is an agent for preventing, improving and/or treating oral diseases and discomforts by use of the bacterial strain.
An agent for preventing and/or treating an oral disease, containing, as an active ingredient, at least one lactic acid bacterium selected from *Lactobacillus crispatus, Lactobacillus fermentum, Lactobacillus gasseri*, and *Streptococcus mitis* and having all of the following properties (1) to (6):
(1) having no ability to produce a volatile sulfur compound (VSC);
(2) having no ability to produce water-insoluble glucan;
(3) having adhesiveness to a tooth surface and/or an oral cell;
(4) having a growth inhibitory effect on a bad breath-causing bacterium and/or a periodontal pathogen;
(5) having no causative role in infective endocarditis; and
(6) having no cariogenicity.

22 Claims, 7 Drawing Sheets

(56) References Cited

OTHER PUBLICATIONS

Tonzetich, J., "Direct Gas Chromatographic Analysis of Sulphur Compounds in Mouth Air in Man", Archs Oral Biol, vol. 16, pp. 587-597, (1971).
Tonzetich, J., "Oral malodour: an indicator of health status and oral cleanliness", Int. Dent. J, vol. 28, No. 3, pp. 309-319, (1978).
Shibuya, K., "Constituents and Origins of Physiological Malodor", J. Dent. Hlth., vol. 51, No. 5, pp. 778-792, (2001) (with English abstract and partial English translation).
"Bad breath makes periodontal disease severer?", Niigata Dental Journal, vol. 32, No. 2, Total 3 Pages, (2002) (with English abstract and partial English translation).
Douglas, C. W. I. et al., "Identity of Viridans streptococci isolated from cases of infective endocarditis", J. Med. Microbiol, vol. 39, pp. 179-182, (1993).
Cannon, J. P. et al., "Pathogenic relevance of Lactobacillus: a retrospective review of over 200 cases", Eur J Clin Microbiol Infect Dis, vol. 24, pp. 31-40, (2005).
Salvana, E. M. T. et al., "Lactobacillus endocarditis: Case report and review of cases reported since 1992", Journal of Infection, vol. 53, pp. e5-e10, (2006).
International Search Report dated Sep. 11, 2012 in PCT/JP12/069916 Filed Aug. 3, 2012.

SEQUENCE LISTING

```
<160> NUMBER OF SEQ ID NOS: 17

<210> SEQ ID NO 1
<211> LENGTH: 19
<212> TYPE: DNA
<213> ORGANISM: Artificial sequence
<220> FEATURE:
<223> OTHER INFORMATION: Primer sequence for amplifying a chromosome DNA
``` region

<400> SEQUENCE: 1
gcytaayaca tgcaagtmg                                               19

<210> SEQ ID NO 2
<211> LENGTH: 20
<212> TYPE: DNA
<213> ORGANISM: Artificial sequence
<220> FEATURE:
<223> OTHER INFORMATION: Primer sequence for amplifying a chromosome DNA
      region

<400> SEQUENCE: 2
aaggaggtga tccarccgca                                              20

<210> SEQ ID NO 3
<211> LENGTH: 15
<212> TYPE: DNA
<213> ORGANISM: Artificial sequence
<220> FEATURE:
<223> OTHER INFORMATION: Primer sequence for amplifying a chromosome DNA
      region

<400> SEQUENCE: 3
accgcggctg ctggc                                                   15

<210> SEQ ID NO 4
<211> LENGTH: 24
<212> TYPE: DNA
<213> ORGANISM: Artificial sequence
<220> FEATURE:
<223> OTHER INFORMATION: Primer sequence for amplifying a chromosome DNA
      region

<400> SEQUENCE: 4
gcacatcgtt atagtgaacg gcgc                                         24

<210> SEQ ID NO 5
<211> LENGTH: 24
<212> TYPE: DNA
<213> ORGANISM: Artificial sequence
<220> FEATURE:
<223> OTHER INFORMATION: Primer sequence for amplifying a chromosome DNA
      region

<400> SEQUENCE: 5
cacatcgtta tagtgaacgg cgct                                         24

<210> SEQ ID NO 6
<211> LENGTH: 27
<212> TYPE: DNA
<213> ORGANISM: Artificial sequence
<220> FEATURE:
<223> OTHER INFORMATION: Primer sequence for amplifying a chromosome DNA
      region

<400> SEQUENCE: 6
acggttcaat acttctaaca catccgc                                      27

<210> SEQ ID NO 7
<211> LENGTH: 25
<212> TYPE: DNA
<213> ORGANISM: Artificial sequence
<220> FEATURE:
<223> OTHER INFORMATION: Primer sequence for amplifying a chromosome DNA
      region -continued

```
<400> SEQUENCE: 7
acacatccgc ttgatcttgt tgttc                                              25

<210> SEQ ID NO 8
<211> LENGTH: 26
<212> TYPE: DNA
<213> ORGANISM: Artificial sequence
<220> FEATURE:
<223> OTHER INFORMATION: Primer sequence for amplifying a chromosome DNA
      region

<400> SEQUENCE: 8
gtagaaacca agttttaagg tctatg                                             26

<210> SEQ ID NO 9
<211> LENGTH: 20
<212> TYPE: DNA
<213> ORGANISM: Artificial sequence
<220> FEATURE:
<223> OTHER INFORMATION: Primer sequence for amplifying a chromosome DNA
      region

<400> SEQUENCE: 9
ttggttgggt taccgtcaac                                                    20

<210> SEQ ID NO 10
<211> LENGTH: 24
<212> TYPE: DNA
<213> ORGANISM: Artificial sequence
<220> FEATURE:
<223> OTHER INFORMATION: Primer sequence for amplifying a chromosome DNA
      region

<400> SEQUENCE: 10
ctttcactag tggagtgtat ttac                                               24

<210> SEQ ID NO 11
<211> LENGTH: 26
<212> TYPE: DNA
<213> ORGANISM: Artificial sequence
<220> FEATURE:
<223> OTHER INFORMATION: Primer sequence for amplifying a chromosome DNA
      region

<400> SEQUENCE: 11
gtctttcact agtggagtgt atttac                                             26

<210> SEQ ID NO 12
<211> LENGTH: 26
<212> TYPE: DNA
<213> ORGANISM: Artificial sequence
<220> FEATURE:
<223> OTHER INFORMATION: Primer sequence for amplifying a chromosome DNA
      region

<400> SEQUENCE: 12
ctttcactag tggagtgtat ttactc                                             26

<210> SEQ ID NO 13
<211> LENGTH: 20
<212> TYPE: DNA
<213> ORGANISM: Artificial sequence
<220> FEATURE:
<223> OTHER INFORMATION: Primer sequence for amplifying a chromosome DNA
      region
```

```
<400> SEQUENCE: 13
gttgacggta acccaaccaa                                             20

<210> SEQ ID NO 14
<211> LENGTH: 24
<212> TYPE: DNA
<213> ORGANISM: Artificial sequence
<220> FEATURE:
<223> OTHER INFORMATION: Primer sequence for amplifying a chromosome DNA
      region

<400> SEQUENCE: 14
gtaaatacac tccactagtg aaag                                        24

<210> SEQ ID NO 15
<211> LENGTH: 26
<212> TYPE: DNA
<213> ORGANISM: Artificial sequence
<220> FEATURE:
<223> OTHER INFORMATION: Primer sequence for amplifying a chromosome DNA
      region

<400> SEQUENCE: 15
gtaaatacac tccactagtg aaagac                                      26

<210> SEQ ID NO 16
<211> LENGTH: 26
<212> TYPE: DNA
<213> ORGANISM: Artificial sequence
<220> FEATURE:
<223> OTHER INFORMATION: Primer sequence for amplifying a chromosome DNA
      region

<400> SEQUENCE: 16
gagtaaatac actccactag tgaaag                                      26

<210> SEQ ID NO 17
<211> LENGTH: 25
<212> TYPE: DNA
<213> ORGANISM: Artificial sequence
<220> FEATURE:
<223> OTHER INFORMATION: Primer sequence for amplifying a chromosome DNA
      region

<400> SEQUENCE: 17
ttaaggtcta tggaaacaac tccaa                                       25
```

PROPHYLACTIC OR THERAPEUTIC AGENT FOR ORAL DISEASES

TECHNICAL FIELD

The present invention relates to an agent for preventing, improving and/or treating oral diseases and discomforts such as caries, periodontal diseases, and bad breath.

BACKGROUND ART

It is pointed out that bad breath is invisible but important from an aesthetic point of view and for leading a comfortable personal life and social life. As a result of quantitatively evaluating the effect of bad breath on oral QOL (quality of life), it is reported that the involvement of bad breath is more significant than physical appearance (Non Patent Document 1). It is further concerned that bad breath is a factor which makes it difficult to take care of aged persons in Japan where society is rapidly aging (Non Patent Document 2).

Bad breath is mainly due to three types of volatile sulfur compounds (VSCs), namely, hydrogen sulfide, methyl mercaptan, and dimethyl sulfide (Non Patent Documents 3 and 4). It is considered that VSCs are generated through the decomposition of cysteine, methionine, and the like contained in desquamated epithelial cells, leucocyte debris, food, and the like in the oral cavity by oral bacteria. It is reported, in culture tests of oral bacteria, that periodontal pathogens belonging to the genus *Fusobacterium, Porphyromonas, Veillonella, Spirochaeta*, and the like produce a large amount of VSC (Non Patent Document 5). In addition, it is also elucidated that *Lactobacillus olis* strain isolated from an oral cavity has a strong ability to produce VSCs. Since VSCs themselves have not only a significantly unpleasant odor but also toxicity to a living tissue even at a low concentration, it is also reported that VSCs are substances responsible for bad breath as well as a highly possible factor of exacerbating the pathological conditions of periodontal diseases (Non Patent Document 6). Thus, suppressing production of VSCs by oral bacteria, particularly periodontal pathogens, thereby preventing or improving bad breath is important not only for improving QOL but also for keeping a healthy oral cavity.

Recently, attempts have been made to apply probiotic technologies also to oral cavities and it is reported that, for example, *Lactobacillus salivarius* TI 2711 strain (Patent Document 1) is effective for bad breath, caries, periodontal diseases, oral infections, and the like.

CITATION LIST

Patent Document

Patent Document 1: JP-B-4203855

Non Patent Document

Non Patent Document 1: Jpn J Public Health, 49, 2002, p298
Non Patent Document 2: Institute for Health Economics and Policy, annual report of investigations and researches (1995)
Non Patent Document 3: Arch Oral Biol, 16, 1971: 587-597
Non Patent Document 4: Int. Dent. J, 28, 1978: 309-319
Non Patent Document 5: J Dent Hlth, 51, 2001, p778-792
Non Patent Document 6: Niigata Dental Journal, 32, 2002, p309-310
Non Patent Document 7: J Med Microbiol, 39, 1991: 179-182
Non Patent Document 8: Eur J Clin Microbiol Infect Dis, 24, 2005: 31-40
Non Patent Document 9: Journal of Infection, 53, 2006: e5-e10

SUMMARY OF THE INVENTION

Problems to be Solved by the Invention

Meanwhile, it is pointed out that oral bacteria belonging to the genus *Lactobacillus* and *Streptococcus* may be one of the causes of caries and infective endocarditis. *Streptococcus sobrinus* is known as a cariogenic bacterium and the harmful effect of the bacterium is stronger than *Streptococcus mutans*. Thus, *Streptococcus sobrinus* is a concern as a cause of caries in the clinical field. Furthermore, the most frequently detected causative microorganisms of infective endocarditis are genus *Streptococcus* such as *Streptococcus sanguinis* and *Streptococcus oralis* in the oral cavity (Non Patent Document 7). Of the bacteria belonging to the genus *Lactobacillus*, some strains are reported to induce endocarditis (Non Patent Documents 8 and 9).

Accordingly, it is desired that bacteria used for keeping a healthy oral flora are capable of suppressing VSC production and in addition, have no cariogenicity and no causative role in infective endocarditis. Unfortunately, a safe bacterium having such properties has not yet been reported up to present.

Therefore, an object of the present invention is to provide a novel lactic acid bacterium strain, which is capable of suppressing the production of volatile sulfur compounds by oral bacteria, has no cariogenicity and no causative role in infective endocarditis, and is safe for the oral cavity, and to provide an agent for preventing, improving and/or treating oral diseases and discomforts by the use of the bacterial strain.

Means for Solving the Problems

The present inventors conducted intensive studies on oral microorganisms. As a result, they found that specific lactic acid bacteria belonging to *Lactobacillus crispatus, Lactobacillus fermentum, Lactobacillus gasseri*, and *Streptococcus mitis* have strong adhesiveness to tooth surfaces and oral cells, and growth inhibitory effects on periodontal pathogens which are also bad breath-causing bacteria, thereby successfully suppressing VSC production, and that the lactic acid bacteria themselves produce neither VSC nor water-insoluble glucan. They also found that since the lactic acid bacteria have no cariogenicity and no causative role in infective endocarditis, they are useful as bacteria for keeping a healthy oral flora. Based on the findings, the present invention was achieved.

Accordingly, the present invention provides an agent for preventing and/or treating an oral disease, containing, as an active ingredient, at least one lactic acid bacterium selected from *Lactobacillus crispatus, Lactobacillus fermentum, Lactobacillus gasseri*, and *Streptococcus mitis* and having all of the following properties (1) to (6):

(1) having no ability to produce a volatile sulfur compound (VSC);
(2) having no ability to produce water-insoluble glucan;
(3) having adhesiveness to a tooth surface and/or an oral cell;

(4) having a growth inhibitory effect on a bad breath-causing bacterium and/or a periodontal pathogen;

(5) having no causative role in infective endocarditis; and (6) having no cariogenicity.

The present invention also provides an agent for preventing and/or improving bad breath, containing, as an active ingredient, at least one lactic acid bacterium selected from *Lactobacillus crispatus, Lactobacillus fermentum, Lactobacillus gasseri*, and *Streptococcus mitis* and having all of the following properties (1) to (6):

(1) having no ability to produce a volatile sulfur compound (VSC);

(2) having no ability to produce water-insoluble glucan;

(3) having adhesiveness to a tooth surface and/or an oral cell;

(4) having a growth inhibitory effect on a bad breath-causing bacterium and/or a periodontal pathogen;

(5) having no causative role in infective endocarditis; and (6) having no cariogenicity.

The present invention also provides the lactic acid bacterium designated as *Lactobacillus crispatus* YIT 12319 and deposited under FERM BP-11500, the lactic acid bacterium designated as *Lactobacillus fermentum* YIT 12320 and deposited under FERM BP-11501, the lactic acid bacterium designated as *Lactobacillus gasseri* YIT 12321 and deposited under FERM BP-11502, or the lactic acid bacterium designated as *Streptococcus mitis* YIT 12322 and deposited under FERM BP-11503.

The present invention also provides a food and drink containing the aforementioned lactic acid bacterium.

The present invention also provides an oral composition containing the aforementioned lactic acid bacterium.

The present invention also provides use of at least one lactic acid bacterium selected from *Lactobacillus crispatus, Lactobacillus fermentum, Lactobacillus gasseri*, and *Streptococcus mitis* and having all of the following properties (1) to (6), for producing an agent for preventing and/or treating an oral disease:

(1) having no ability to produce a volatile sulfur compound (VSC);

(2) having no ability to produce water-insoluble glucan;

(3) having adhesiveness to a tooth surface and/or an oral cell;

(4) having a growth inhibitory effect on a bad breath-causing bacterium and/or a periodontal pathogen;

(5) having no causative role in infective endocarditis; and (6) having no cariogenicity.

The present invention also provides use of at least one lactic acid bacterium selected from *Lactobacillus crispatus, Lactobacillus fermentum, Lactobacillus gasseri*, and *Streptococcus mitis* and having all of the following properties (1) to (6), for producing an agent for preventing and/or improving bad breath:

(1) having no ability to produce a volatile sulfur compound (VSC);

(2) having no ability to produce water-insoluble glucan;

(3) having adhesiveness to a tooth surface and/or an oral cell;

(4) having a growth inhibitory effect on a bad breath-causing bacterium and/or a periodontal pathogen;

(5) having no causative role in infective endocarditis; and (6) having no cariogenicity.

The present invention also provides a method for preventing and/or treating an oral disease, comprising administering an effective amount of at least one lactic acid bacterium selected from *Lactobacillus crispatus, Lactobacillus fermentum, Lactobacillus gasseri*, and *Streptococcus mitis* and having all of the following properties (1) to (6):

(1) having no ability to produce a volatile sulfur compound (VSC);

(2) having no ability to produce water-insoluble glucan;

(3) having adhesiveness to a tooth surface and/or an oral cell;

(4) having a growth inhibitory effect on a bad breath-causing bacterium and/or a periodontal pathogen;

(5) having no causative role in infective endocarditis; and (6) having no cariogenicity.

The present invention also provides a method for preventing and/or improving bad breath, comprising administering an effective amount of at least one lactic acid bacterium selected from *Lactobacillus crispatus, Lactobacillus fermentum, Lactobacillus gasseri*, and *Streptococcus mitis* and having all of the following properties (1) to (6):

(1) having no ability to produce a volatile sulfur compound (VSC);

(2) having no ability to produce water-insoluble glucan;

(3) having adhesiveness to a tooth surface and/or an oral cell;

(4) having a growth inhibitory effect on a bad breath-causing bacterium and/or a periodontal pathogen;

(5) having no causative role in infective endocarditis; and (6) having no cariogenicity.

The present invention also provides at least one lactic acid bacterium selected from *Lactobacillus crispatus, Lactobacillus fermentum, Lactobacillus gasseri*, and *Streptococcus mitis* and having all of the following properties (1) to (6), for use in preventing and/or treating an oral disease:

(1) having no ability to produce a volatile sulfur compound (VSC);

(2) having no ability to produce water-insoluble glucan;

(3) having adhesiveness to a tooth surface and/or an oral cell;

(4) having a growth inhibitory effect on a bad breath-causing bacterium and/or a periodontal pathogen;

(5) having no causative role in infective endocarditis; and (6) having no cariogenicity.

The present invention also provides at least one lactic acid bacterium selected from *Lactobacillus crispatus, Lactobacillus fermentum, Lactobacillus gasseri*, and *Streptococcus mitis* and having all of the following properties (1) to (6), for use in preventing and/or improving bad breath:

(1) having no ability to produce a volatile sulfur compound (VSC);

(2) having no ability to produce water-insoluble glucan;

(3) having adhesiveness to a tooth surface and/or an oral cell;

(4) having a growth inhibitory effect on a bad breath-causing bacterium and/or a periodontal pathogen;

(5) having no causative role in infective endocarditis; and (6) having no cariogenicity.

The present invention also provides a primer or probe specific to *Lactobacillus crispatus* YIT 12319 (FERM BP-11500), comprising a base sequence selected from SEQ ID NOs: 4 to 8 or a complementary sequence thereto.

The present invention also provides a primer pair specific to *Lactobacillus crispatus* YIT 12319 (FERM BP-11500), comprising a base sequence selected from SEQ ID NOs: 4 and 8, SEQ ID NOs: 5 and 8, SEQ ID NOs: 6 and 8, and SEQ ID NOs: 7 and 8, or a complementary sequence thereto.

The present invention also provides a method for detecting *Lactobacillus crispatus* YIT 12319 (FERM BP-11500), comprising using the primer, the primer pair, or the probe.

Effects of the Invention

The lactic acid bacteria in the present invention colonize on tooth surfaces and in the oral cavity and have growth inhibitory effects on cariogenic bacteria and periodontal pathogens which are also bad breath-causing bacteria; whereas the lactic acid bacteria have no ability to produce a VSC or water-insoluble glucan and have no cariogenicity and no causative role in infective endocarditis. Therefore, the lactic acid bacteria are useful as pharmaceutical agents, foods and drinks, pet foods, oral compositions, and the like for keeping a healthy oral flora, thereby preventing, improving, or treating various oral diseases or discomforts such as caries, periodontal diseases, and bad breath.

MODES FOR CARRYING OUT THE INVENTION

Figure 1:
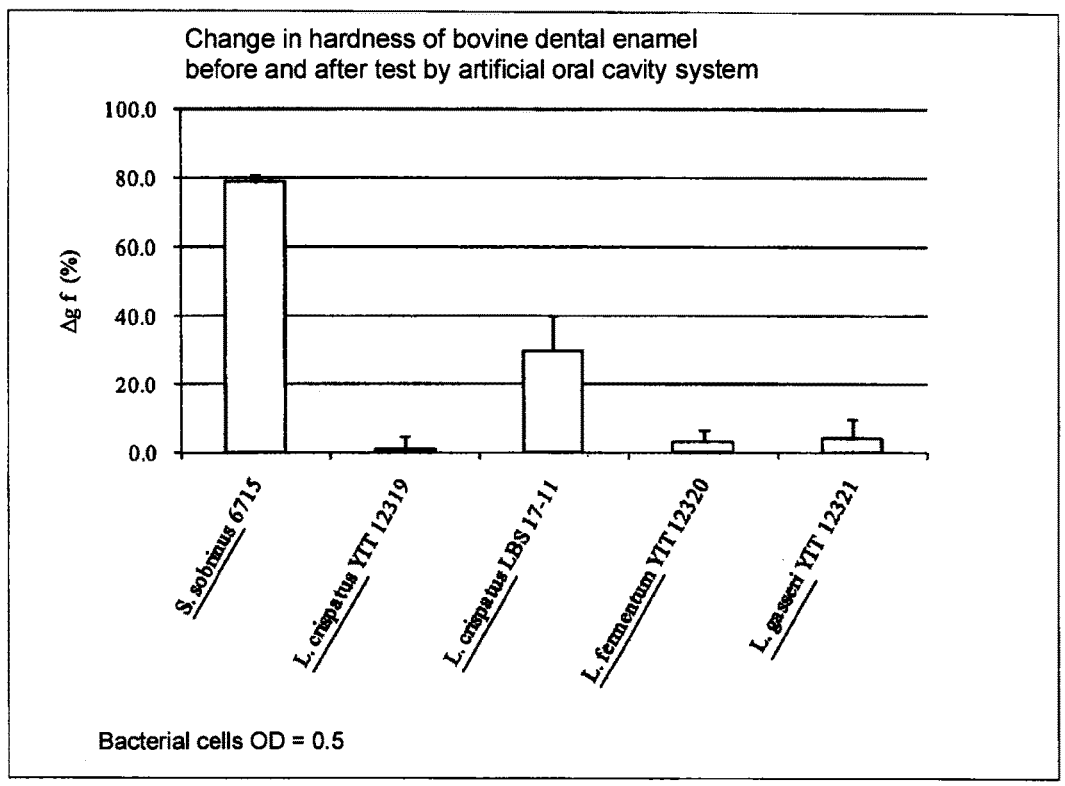
FIG. 1 is a graph showing the change in the hardness of bovine dental enamel which was exposed with YIT 12319 to 12321.

Examples of the lactic acid bacterium to be used in the present invention include lactic acid bacterium strains belonging to *Lactobacillus crispatus, Lactobacillus fermentum, Lactobacillus gasseri*, and *Streptococcus mitis*. These bacterial strains may be used singly or two or more thereof may be used in combination.

More specifically, the lactic acid bacterium designated as *Lactobacillus crispatus* YIT 12319 and deposited under FERM BP-11500 at the International Patent Organism Depositary, Incorporated Administrative Agency National Institute of Technology and Evaluation (address: Central 6, 1-1-1 Higashi, Tsukuba, Ibaraki, Japan) as of Apr. 28, 2011 (the same shall apply hereinafter); the lactic acid bacterium designated as *Lactobacillus fermentum* YIT 12320 and deposited under FERM BP-11501; the lactic acid bacterium designated as *Lactobacillus gasseri* YIT 12321 and deposited under FERM BP-11502; and the lactic acid bacterium designated as *Streptococcus mitis* YIT 12322 and deposited under FERM BP-11503 are mentioned. Examples of the lactic acid bacteria include progeny strains obtained from these bacteria as parent strains (including natural variants, variants obtained by mutation treatment, variants by gene manipulation, etc.).

The aforementioned *Lactobacillus crispatus* YIT 12319 (FERM BP-11500), *Lactobacillus fermentum* YIT 12320 (FERM BP-11501), *Lactobacillus gasseri* YIT 12321 (FERM BP-11502), and *Streptococcus mitis* YIT 12322 (FERM BP-11503) were isolated from human oral cavities for the first time by the present inventors, as shown later in Examples and identified as bacterial strains belonging to *Lactobacillus crispatus, Lactobacillus fermentum, Lactobacillus gasseri*, and *Streptococcus mitis*, respectively, as a result of homology analysis of 16S-rDNA gene sequences. It was found that these lactic acid bacterium strains are novel bacterial strains since they have the following characteristic properties (1) to (6):

(1) having no ability to produce a volatile sulfur compound (VSC);

(2) having no ability to produce water-insoluble glucan;

(3) having adhesiveness to tooth surfaces and/or oral cells;

(4) having a growth inhibitory effect on bad breath-causing bacteria and/or periodontal pathogens;

(5) having no causative role in infective endocarditis; and (6) having no cariogenicity.

Furthermore, *Lactobacillus gasseri* YIT 12321 (FERM BP-11502) was confirmed to have the following property (7):

(7) utilizing no sucrose.

Note that, in the specification, the property (1) "having no ability to produce a volatile sulfur compound (VSC)" refers to the ability to produce VSC being +/− (HSS<0.70 μg/10 ml/O.D., $CH_3SH$<1.17 μg/10 ml/O.D.) and more preferably, being − (lower detection limit value or less) in the experiment of Examples hereinbelow described (Test Example 2). A lactic acid bacterium having the property (1) is preferable since it does not produce a VSC, which is a bad breath causing substance as well as a factor of exacerbating the pathological conditions of periodontal diseases.

Furthermore, in the specification, the property (2) "having no ability to produce water-insoluble glucan" refers to the ability to produce water-insoluble glucan being +/− (bacterial cells attached) and more preferably, being − (no production) in the experiment of Examples hereinbelow described (Test Example 3). A lactic acid bacterium having the property (2) is preferable since it does not produce water-insoluble glucan that causes caries.

Furthermore, in the specification, the property (3) "having adhesiveness to tooth surfaces" refers to a rate of adhesion to S-HA being 1.0% or more and more preferably, being 10% or more in the experiment of Examples hereinbelow described (Test Example 5). Furthermore, in the specification, the property (3) "having adhesiveness to oral cells" refers to the rate of adhesion to oral cells being 30 cells/0.16 $mm^2$ or more in total, in the experiment of Examples hereinbelow described (Test Example 6). A lactic acid bacterium having adhesiveness to tooth surfaces or oral cells of property (3) is preferable since the bacterium more easily colonizes in the oral cavity even in a short retention time as is in the case of e.g., oral administration. For the same reason, a lactic acid bacterium having adhesiveness to tooth surfaces and oral cells is more preferable.

Furthermore, in the specification, the property (4) "having a growth inhibitory effect on bad breath-causing bacteria and/or periodontal pathogens" refers to the sum of diameters of inhibition zones being 9 mm or more in the experiment of Examples hereinbelow described (Test Example 7). A lactic acid bacterium having the property (4) is preferable since it exerts excellent prophylactic/therapeutic effects on e.g., bad breath and/or periodontal diseases.

Furthermore, in the specification, the property (5) "having no causative role in infective endocarditis" refers to being negative for causative role in rat endocarditis in the experiment of Examples hereinbelow described (Test Example 8).

A lactic acid bacterium having the property (5) has extremely high safety and can be suitably used as e.g., foods and drinks and oral compositions.

Furthermore, in the specification, the property (6) "having no cariogenicity" refers to the hardness reduction rate of bovine dental enamel after a test in an artificial oral cavity system being less than 5% in the experiment of Examples hereinbelow described (Test Example 9). A lactic acid bacterium having the property (6) is preferable since it does not produce water-insoluble glucan that causes caries and does not decalcify dental enamel.

Moreover, in the specification, the property (7) "utilizing no sucrose" refers to being unable to use sucrose as a growth substrate for bacterial cells in the experiment of Examples hereinbelow described (Test Example 9). A lactic acid bacterium having the property (7) is preferable since the bacterium hardly produces lactic acid and thus reduces the risk of caries.

In the present invention, the bacterial cells of the above lactic acid bacteria are cultured in accordance with a conventional method for culturing lactic acid bacteria and bacterial cells isolated from the resultant cultured product by a cell collection means such as centrifugation can be directly used. Alternatively, after completion of culture, the cultured product of the lactic acid bacterium can be directly used or the culture medium can be concentrated and used as a concentrate. Furthermore, not only viable bacterial cells but also processed bacterial cells may be used. The processed bacterial cells are not particularly limited as long as they can be obtained by a conventional method. Examples of the processed bacterial cells include killed bacterial cells obtained through heat treatment, treatment with a drug such as an antibiotic substance, treatment with a chemical substance such as formalin, treatment with UV rays, or treatment with radiation such as γ rays, lyophilized products thereof, and cultured products containing these; a suspension of bacterial cells disrupted by e.g., ultrasonic waves, a suspension of bacterial cells treated with an enzyme, and a solid residue isolated from these by solid/liquid separation means such as filtration and centrifugation; a suspension of treated bacterial cells, from which cell walls are removed by enzymatic or mechanical means, a concentrate thereof, a diluted product of these, and dried product of these; a nucleic acid containing fraction obtained by lysing bacterial cells with the aid of e.g., a surfactant, followed by precipitation with e.g., ethanol; and a product obtained by subjecting a suspension of bacterial cells disrupted by e.g., ultrasonic waves, or a suspension of bacterial cells treated with an enzyme as described above to separation and purification treatments with a separation means such as various chromatography methods.

The medium for culturing the lactic acid bacteria is not particularly limited and various media can be used.

For example, a nutrition medium conventionally used for the proliferation of a lactic acid bacterium that contains carbon sources such as glucose, fructose, galactose, and sucrose, inorganic salts such as monopotassium phosphate, dipotassium phosphate, magnesium sulfate, sodium sulfite, sodium thiosulfate, and ammonium phosphate, organic nutrition sources such as polypeptone, yeast extract, and corn steep liquor, and, if necessary, various amino acids and vitamins can be used. A milk medium containing milk can also be used.

Any culture conditions may be employed as long as the bacterial cells satisfactorily grow. The culture method is not particularly limited. Examples thereof include aeration culture, anaerobic culture, spinner culture, shaking culture, and static culture. In consideration of productivity, it is preferable to perform static culture under aerobic conditions.

Furthermore, the culture temperature is usually 10 to 50° C. and preferably 25 to 37° C. The culture time is usually 6 hours to 3 days, and preferably 8 hours to 3 days.

Furthermore, the pH (25° C.) of a medium is 3 to 10 and preferably 5 to 8. Examples of buffer agents to adjust pH of a medium include salts of organic acids such as carbonic acid, acetic acid, citric acid, fumaric acid, malic acid, lactic acid, gluconic acid, and tartaric acid; salts of inorganic acids such as phosphoric acid, hydrochloric acid, and sulfuric acid; hydroxides such as sodium hydroxide; and ammonia or ammonia water. These may be used alone or in combination of two or more thereof.

The "oral diseases" in the phrase "the agent for preventing and/or treating oral diseases" of the present invention refer to the oral diseases caused by pathogenic oral bacteria such as cariogenic bacteria, periodontal pathogens, and candida. Examples of the oral diseases include caries, periodontal diseases such as gingivitis and periodontitis, and oral candidiasis. As the oral diseases, periodontal diseases such as gingivitis and periodontitis are preferably mentioned.

Examples of the cariogenic bacteria include *Streptococcus mutans* and *Streptococcus sobrinus*. Examples of the periodontal pathogens include *Porphyromonas gingivalis, Prevotella intermedia, Treponema denticola, Tannerella forsythia, Aggregatibacter actinomycetemcomitans*, and *Fusobacterium nucleatum*. Examples of oral candidiasis causing bacteria include *Candida albicans*.

Examples of the "bad breath-causing bacteria" relating to the agent for preventing and/or improving bad breath of the present invention include *Porphyromonas gingivalis, Fusobacterium nucleatum, Prevotella intermedia, Treponema denticola*, and *Veillonella dispar*.

As shown later in Examples, the lactic acid bacteria of the present invention adhere to tooth surfaces and the sites in an oral cavity and have a growth inhibitory effect on bad breath-causing bacteria and periodontal pathogens such as *Porphyromonas gingivalis, Prevotella intermedia*, and *Aggregatibacter actinomycetemcomitans*. Furthermore, it was confirmed that the lactic acid bacteria of the present invention produce neither VSCs that cause bad breath nor water-insoluble glucan that causes caries, and additionally, the lactic acid bacteria do not decalcify dental enamel or cause infective endocarditis.

In short, the lactic acid bacteria of the present invention contribute to keeping a healthy oral bacterial flora and can be used as pharmaceutical agents, foods and drinks, pet foods, oral compositions, and the like, for preventing, improving, or treating various oral diseases or discomforts such as caries, periodontal diseases such as gingivitis and periodontitis, oral candidiasis, and bad breath, caused by pathogenic oral bacteria.

When the lactic acid bacteria of the present invention are used as a pharmaceutical agent, examples of the dosage form of the oral preparations include a tablet, a capsule, a granule, a sugar-coated tablet, a pill, a fine granule, a powder, a sustained-release preparation, a suspension, an emulsion, a syrup, a lyophilized agent, a liquid, and an elixir.

The preparation can be produced by a conventional method. Furthermore, the lactic acid bacterium of the present invention may be used singly or in combination with a pharmaceutically acceptable carrier. Examples of the carrier include excipients such as lactose, refined sugar, sodium chloride, glucose, urea, starch, calcium carbonate, kaolin, microcrystalline cellulose, and silicic acid; binding agents such as starch, dextrin, powdered acacia, gelatin, methyl-cellulose, hydroxypropylcellulose, microcrystalline cellulose, ethylcellulose, polyvinylpyrrolidone, and macrogol; disintegrants such as hydroxypropyl starch, sodium carboxymethylcellulose, calcium carboxymethylcellulose, carboxymetylcellulose, and low-substitution hydroxypropylcellulose; surfactants such as sodium lauryl sulfate, soybean lecithin, sucrose fatty acid ester, and polysorbate 80; lubricants such as talc, wax, hydrogenated vegetable oil, magnesium stearate, calcium stearate, aluminum stearate, and polyethylene glycol; fluidity accelerators such as light anhydrous silicic acid, dried aluminum hydroxide gel, synthetic aluminum silicate, and magnesium silicate; and diluents such as distilled water for injection, physiological saline, aqueous glucose solution, olive oil, sesame oil, peanut oil, soybean oil, corn oil, propylene glycol, and polyethylene glycol. Furthermore, if necessary, additives routinely used such as a flavoring agent, a coloring agent, a flavor, a disinfectant, an osmotic adjuster, a pH adjuster, an emulsifier, an absorption aid, an antioxidant, a thickener, and an isotonizing agent can be appropriately added.

Furthermore, when the lactic acid bacteria of the present invention are used as a food and drink, a pet food, and the like, if necessary, various nutrient components can be added to the lactic acid bacteria of the present invention and then added to the food and drink, and the like. The food and drink, and the like, can be used, for example, as food for specified health use or foodstuff useful for preventing or improving caries, periodontal diseases, and bad breath. A label for expressing such an effect may be attached to these foods and drinks or containers thereof.

As the form of foods and drinks, products obtained by appropriately adding acceptable additives as food and drink to the lactic acid bacteria and molding the mixture into forms suitable for eating by the use of conventional means, such as a granule, a powder, a tablet, a capsule, and paste may be used. Alternatively, products obtained by adding the lactic acid bacteria to various foods, for example, processed meat products such as ham and sausage: processed seafood products such as cooked minced fish (kamaboko) or fish sausage (chikuwa); bread, confectionary, butter, powdered milk, and fermented food and drink, or products obtained by adding the lactic acid bacterifum to water, fruit juice, milk, soft drink, tea drink, and the like, may be used. Of them, fermented products such as fermented milk, fermented drink (lactic acid bacteria beverage), fermented soymilk, fermented fruit juice, and fermented plant extracts and supplements such as tablets and capsules, containing the lactic acid bacteria as an active ingredient, are preferable.

The fermented products can be produced in accordance with conventional methods. For example, fermented milk is produced by inoculating the lactic acid bacterium to a sterilized milk medium, followed by culturing; homogenizing the culture solution to obtain a fermented milk base; then adding a syrup solution separately prepared to the base, followed by mixing; homogenizing the mixture by e.g., a homogenizer; and further adding flavor to the resultant to obtain a final product. The fermented milk thus obtained may be any of plane type, soft type, fruit flavor type, solid type, liquid type, and the like.

In using the lactic acid bacterium as an oral composition, examples of a form of the composition include a mouth rinse, a mouth wash, a toothpaste, a powder toothpaste, a liquid tooth paste, an oral ointment, a gel, a tablet, a granule, a fine granule, a gummi jelly, a troche, a tablet, a capsule, a candy, and a chewing gum. Preferably, a toothpaste, a mouth rinse, a gummi jelly, a troche, and a tablet are mentioned.

The content of the lactic acid bacterium of the present invention in the aforementioned pharmaceutical agents, foods and drinks, pet foods, oral compositions, and the like, is not particularly limited and may be appropriately controlled in accordance with the dose or amount of intake per day. For example, in the case of a liquid form, the concentration of lactic acid bacterium cells is preferably $1 \times 10^6$ CFU/mL to $1 \times 10^8$ CFU/mL. In the case of a solid form, the concentration is preferably $1 \times 10^7$ CFU/g to $1 \times 10^{10}$ CFU/g.

There is no strict limitation on the dose or amount of intake of the lactic acid bacteria of the present invention to be used. Since the effect varies depending upon the conditions such as the subject and the disease to be applied, it is desired to appropriately set the dose or amount of intake; however, the dose containing $1 \times 10^3$ CFU or more per day as the bacterial count of the lactic acid bacteria is preferable, $1 \times 10^3$ to $1 \times 10^{13}$ CFU per day is more preferable, and $1 \times 10^6$ to $1 \times 10^{10}$ CFU per day is particularly preferable.

As a result of the analysis of the genomic DNAs of *Lactobacillus crispatus* YIT12319 and other *Lactobacillus crispatus* strains, it was found that a base sequence selected from SEQ ID NOs: 4 to 8 is specific to *Lactobacillus crispatus* YIT 12319, and when probes or primers having these base sequences are used, genes of *Lactobacillus crispatus* YIT 12319 can be specifically detected or amplified.

The probe or primer of the present invention has a base sequence selected from SEQ ID NOs: 4 to 8 or a complementary sequence thereto, and specific to the bacterial strain *Lactobacillus crispatus* YIT 12319 (FERM BP-11500).

As the primer, a primer having a base sequence selected from SEQ ID NO: 4 and SEQ ID NO: 5, SEQ ID NOs: 4 and 6, SEQ ID NOs: 4 and 7, and SEQ ID NOs: 4 and 8 or a complementary sequence thereto is more preferable since the specificity of the primer to *Lactobacillus crispatus* YIT 12319 (FERM BP-11500) is high.

By performing PCR using DNA derived from the *Lactobacillus crispatus* YIT 12319 (FERM BP-11500) that is extracted from a specimen and using the probe or primer, it is possible to quickly and simply identify, analyze, and detect the bacterial strain without intricate operations such as confirmation of physiological and biochemical characteristics.

EXAMPLES

The present invention will be more specifically described by way of Examples; however, the present invention is not limited by these Examples.

Test Example 1

Separation of Oral Bacteria

1) Test Subject and Collection of Sample

From 56 subjects (34 males, 22 females, from 25 to 66 years old, averaged age: 40.6), the plaque (including saliva) and the tongue coat were separately collected. These oral samples collected were stood still on ice until use. For isolating bacterial cells, these samples were mixed in equal amounts and 300 μL of the mixture was added to 2.7 mL of sterilized anaerobic transport medium to prepare a $10^{-1}$ dilution solution (aerobic/anaerobic culture, 3.0 mL for each).

2) Culture and Separation of Oral Bacteria

The oral sample was smeared to *Brucella* rabbit hemolysis plate medium (BRU plate medium, Toriputopen (10.0 g), Peputamin (10.0 g), yeast extract (2.0 g), glucose (1.0 g), sodium chloride (5.0 g), acidic sodium sulfite (0.1 g), hemin (5.0 mg), vitamin K1 (1.0 mg), a growth aid solution (10.0 mL), rabbit hemolysate (60.0 mL), agar (15.0 g), pH 7.0) in an anaerobic glove box. To a disposable test tube (FAL-CON2058), a sterilized anaerobic dilution solution (1.8 mL) was dispensed. To the test tube, the $10^{-1}$ dilution solution (200 µL) was added to prepare a $10^{-2}$ dilution solution. Subsequently, the same operation was repeated until a $10^{-10}$ dilution solution was prepared. Each dilution solution (100 µL) was smeared to the plate medium and then cultured in the conditions shown in Table 1.

In the meantime, a sample was smeared to 5.0% sheep blood supplemented TSA plate medium (TSA plate medium, casein peptone (15.0 g), soybean peptone (5.0 g), sodium chloride (5.0 g), sheep defibrinated blood (50.0 mL), agar (15.0 g), DW (1000 mL), pH 7.3); MRS plate medium (Proteose Peptone No. 3 (10.0 g), beef extract (10.0 g), yeast extract (5.0 g), dextrose (20.0 g), polysorbate 80 (1.0 g), ammonium citrate (2.0 g), sodium acetate (5.0 g), magnesium sulfate (0.1 g), manganese sulfate (0.05 g), dipotassium phosphate (2.0 g), agar (15 g), DW (1000 mL)); LBS plate medium (pancreatic digest of casein (10.0 g), yeast extract (5.0 g), monopotassium phosphate (6.0 g), ammonium citrate (2.0 g), dextrose (20.0 g), polysorbate 80 (1.0 g), sodium acetate hydrate (25.0 g), magnesium sulfate (0.575 g), manganese sulfate (0.12 g), ferrous sulfate (0.034 g), agar (15.0 g), Lab-lemco powder (Oxoid) (8 g), sodium acetate, trihydrate (15 g), DW (1000 mL), acetate (3.7 mL)); and Mitis-Salivarius plate medium (MS plate medium, Bacto Tryptose (10 g), Bacto Proteose Peptone No. 3 (5 g), Bacto Proteose Peptone (5 g), Bacto Dextrose (1 g), Bacto Saccharose (50 g), dipotassium phosphate (4 g), trypan blue (0.075 g), Bacto Crystal Violet (0.0008 g), bacto agar (15 g), DW (1000 mL), pH 7.0±0.2), by using a spiral system (automatic plating apparatus) and then cultured in the conditions shown in Table 1.

TABLE 1

Plate medium and culture method

| Name of plate medium | Abbreviation | Culture subject | Culture temperature | Culture period | Culture condition |
|---|---|---|---|---|---|
| Brucella rabbit hemolysis blood | BRU | All anaerobes | 37° C. | 2~3 days | GB[a] |
| 5.0% sheep blood supplemented TSA | TSA | All facultative anaerobes | 37° C. | 2~3 days | Aerobic condition |
| MRS | MRS | Lactic acid bacteria Bifidobacterium | 37° C. | 2~3 days 2~3 days | GP[b] |
| LBS | LBS | Lactobacillus | 37° C. |  | GB |
| Mitis-Salivarius | MS | Streptococcus | 37° C. | 2~3 days | GP |

[a]GB: cultured in anaerobic glove box
[b]GP: cultured in Anaero pack anaerobic system (Mitsubishi Gas Chemical Company, Inc.)

The colony count of oral bacteria grown in each plate medium is shown in Table 2.

Bacterial cells were picked up from colonies different in shape in MRS, MS, and LBS plate media (in the order of the dilution rate of the solution smeared to the plate medium) and grown in MRS or BHI liquid medium (calf brain exudate (12.5 g), bovine cardiac muscle exudate (5.0 g), proteose-peptone (10.0 g), glucose (2.0 g), sodium chloride (5.0 g), disodium hydrogenphosphate (2.5 g), DW (1000 mL), pH 7.4±0.2), and then suspended in a solution of 2×BHI: glycerol=1:1. The suspension was stored at −80° C. and subjected to the following test.

TABLE 2

Colony count of oral bacteria grown in each plate medium

| | Plate media* | | | | |
|---|---|---|---|---|---|
| | BRU | TSA | MRS | MS | LBS |
| Colony count (Log CFU/ oral cavity) | 9.3 ± 0.54 | 8.6 ± 0.27 | 8.4 ± 0.37 | 8.5 ± 0.30 | 4.7 ± 0.95 |
| Detection rate (%) | 100 | 100 | 100 | 100 | 73.9 |

*BRU: all anaerobes, TSA: all facultative anaerobes, MRS: Lactic acid bacterium, Bifidobacterium, MS: genus Streptococcus, LBS: genus Lactobacillus Test Example 2

Evaluation of VSC Production Ability

The cryopreserved bacterial strains isolated in Test Example 1 were used. As the positive control strain, Fusobacterium nucleatum YIT 6069 was used.

Each of the isolated strains was inoculated in MRS liquid medium and anaerobically cultured at 37° C. for 24 hours. The culture solution (0.04 mL) of the bacterial cells was inoculated in 4 mL of a modified GAM liquid medium (peptone (5.0 g), soybean peptone (3.0 g), proteose peptone (5.0 g), digestive serum powder (10.0 g), yeast extract powder (2.5 g), meat extract powder (2.2 g), liver extract powder (1.2 g), glucose (0.5 g), soluble starch (5.0 g), L-tryptophan (0.2 g), L-cysteine hydrochloride (0.3 g), sodium thioglycolate (0.3 g), L-arginine (1.0 g), vitamin K1 (5 mg), hemin (10 mg), potassium dihydrogenphosphate (2.5 g), sodium chloride (3.0 g), DW (1000 mL), pH 7.3) containing 1% D-(+) glucose and 66 mM DL-methionine (final concentration: 500-1,500 µM), and anaerobically cultured at 37° C. Twenty four hours after initiation of the culture, a 6.0 N hydrochloric acid solution (0.16 mL) was added to the culture solution to reduce the pH to 1 or less, thereby stopping the metabolism of the bacteria.

Thereafter, volatile sulfur compounds (VSCs) vaporized in the headspace were analyzed by gas chromatography or Oral Chroma. Note that the medium anaerobically incubated at 37° C. for 24 hours was used as a negative control.

Test Example 3

Evaluation of Water-insoluble Glucan Production Ability

Two inoculate loops of each of the cryopreserved strains isolated in Test Example 1 were inoculated in BHI or MRS liquid medium and anaerobically cultured at 37° C. for 24 hours. The culture solution (0.04 mL) of the bacteria was inoculated in 4 ml of a 1% sucrose-containing HI liquid medium (bovine cardiac muscle exudate (5.0 g), proteose-peptone (10.0 g), glucose (2.0 g), sodium chloride (5.0 g), disodium hydrogenphosphate (2.5 g), DW (1000 mL), pH 7.4±0.2) or a mixture of MRS liquid medium and HI liquid medium (7:3) and anaerobically cultured in the test tube at a tilt with an angle of 45° at 37° C.

The water-insoluble glucan production ability was evaluated based on the amount of glucan adhering to a test-tube wall and adhesive strength. Twenty four hours after the culture, the culture solution was removed from the test tube, PBS (4 mL) was added thereto, and the test tube was gently rotated three times to wash the tube wall. After PBS was removed, the amount of water-insoluble glucan adhering to the test-tube wall was visually evaluated in accordance with the criteria shown in Table 3.

The results of Test Examples 2 and 3 are shown in Table 3. Of the cryopreserved strains isolated in Test Example 1, 241 bacterial strains in total surrounded by the dotted line in Table 3 were selected. Of them, *Streptococcus*-like bacteria isolated from the MRS and MS media were 176 strains and *Lactobacillus*-like bacteria isolated from the LBS medium were 65 strains.

Note that *Fusobacterium nucleatum* YIT 6069 serving as a positive control strain produced VSC depending upon the additive amount of methionine.

TABLE 3

VSC production ability and water-insoluble glucan production ability of isolated bacterial strains (numerical values in table indicate the number of bacterial strains)

|  | Water-insoluble glucan production ability[2] | | | |
|---|---|---|---|---|
|  | − | +/− | + |  |
| VSC production ability[1] |  |  |  |  |
| − | 22 | 47 | 77 | 146 |
| +/− | 72 | 100 | 187 | 359 |
| + | 82 | 125 | 184 | 391 |
|  | 176 | 272 | 448 | 896 |

[1]VSC production ability; − lower detection limit value or less, +/− ($H_2S$ < 0.70 μg/10 ml/O.D., $CH_3SH$ < 1.17 μg/10 ml/O.D.), + produce
[2]Water-insoluble glucan production ability; − not produce, +/− bacterial cells attach, + produce Test Example 4

Identification of Bacterial Species

DNA was extracted by a benzyl chloride method. After completion of culture, bacterial cells were collected by centrifugation at 830×g for 10 minutes. To the bacterial cells, 200 μL of DNA Extraction buffer, 400 μL of benzyl chloride, and 300 mg of glass beads (diameter: 0.1 mm) were added. After shaking by FastPrep (at a speed of 6.5 for 30 seconds), the mixture was centrifuged (20,000×g, 5 minutes, 4° C.). To the resultant supernatant, an equal amount of isopropanol was added and sufficiently stirred. After the supernatant was removed by centrifugation (20,000×g, 10 minutes, 4° C.), 150 μL of 70% ethanol was added. The mixture was centrifuged again and the obtained precipitation was air-dried and dissolved in an appropriate amount of TE (Tris-EDTA). A PCR solution was prepared so as to contain, in a total amount of 25 μL, 3.2 μL of 10×PCR buffer (1×PCR buffer=10 mM Tris-HCl (pH 8.3), 50 mM KCl, 1.5 mM $MgCl_2$), 2.5 μL of 2.5 mM dNTP (deoxynucleotide triphosphate), 0.5 μL of 25 μmol/μL primers (forward primer 63F; SEQ ID NO: 1, reverse primer 15R; SEQ ID NO: 2), 0.5 units of DNA Taq polymerase (Takara Ex Taq hotstart), and 1 μL of 10 ng/mL template DNA. A PCR was performed as follows: 94° C. for 20 seconds; 30 cycles of 94° C. for 20 seconds, 55° C. for 20 seconds, and 72° C. for 90 seconds; and 72° C. for 3 minutes. 16S-rDNA base sequence of the isolated strain was determined by a dye terminator method. The primer for a sequence reaction was 520R (SEQ ID NO: 3). By comparing the sequence homology between the isolated strain and the bacteria registered in the DNA Data Bank of Japan, if the isolated strain showed a homology of 98% or more with a reference species, the isolated strain was identified as the same species as the reference species. The primers used are shown in Table 4. 16S-rDNAs of a eubacterium and an archaebacterium have about 10 highly conserved regions on both ends or internal regions. By using primers designed based on these sequences such as 63F, 15R, 520R and others, the gene can be amplified and the sequence can be analyzed regardless of the bacterial species.

TABLE 4

Characteristics of primer

| Primer | Base sequence (5'-3') | Target |
|---|---|---|
| 63F | GCYTAAYACATGCAAGTMG | All bacteria |
| 520R | ACCGCGGCTGCTGGC | All bacteria |
| 15R | AAGGAGGTGATCCARCCGCA | All bacteria |

The sequence for primer 63F is SEQ ID NO: 1, The sequence for primer 520R is SEQ ID NO: 3, and the sequence for primer 15R is SEQ ID NO: 2.

As a result of the identification of bacterial species of 241 strains selected in Test Examples 2 and 3 by use of a 16S-rDNA base sequence, the *Streptococcus*-like bacteria were identified mainly as *Streptococcus oralis*, *Streptococcus salivarius*, *Streptococcus mitis*, *Streptococcus sanguinis*, and the like. In addition, of *Lactobacillus*-like bacteria, the most frequently separated species was *Lactobacillus gasseri*.

Test Example 5

Evaluation of Adhesiveness to Tooth Surface

From the 241 strains selected from the results of Test Examples 2 and 3, bacterial strains, which were determined to have a problem in safety as the results of the identification test, were removed and the remaining strains were used in the following test.

Sample preparation and evaluation for adhesiveness to hydroxyapatite (HA) were performed in accordance with the method of Gibbons et al. (Gibbons, R. J., E. C. Moreno, and D. M. Spinell "Model delineating the effect of a salivary pellicle on the adsorption of *Streptococcus mitior* onto hydroxyapatite." Infect. Immun. 1976: 14: 1109-1112).

Each isolated strain was inoculated in MRS liquid medium (4 mL) and cultured for 24 hours. After completion of culture, the culture solution was centrifuged (1,912×g, 10 minutes, 4.0° C.) and washed twice with PBS. The bacterial cells were diluted with PBS so as to obtain an absorbance of 1.0 at 550 nm and the resultant bacterial suspension was used in an adhesion test to HA.

The saliva to be used in this test was collected as follows. After gargle with distilled water, subjects chewed the paraffin gum. The saliva secreted by stimuli of chewing was collected in a centrifuge tube, respectively. To inactivate a proteolytic enzyme, the collected saliva was heated at 60° C. for 30 minutes. Then the saliva was centrifuged (10,000×g, 10 minutes, 4.0° C.) to obtain the supernatant. The saliva taken from 5 persons were mixed in equivalent amounts, sterilized by filtration (0.22 µm) and stored at 4° C. until use.

Hydroxyapatite beads (Bio-Rad, 40 µm) (5 mg) were washed with PBS. To the beads, saliva (4 mL) prepared by heating was added and the mixture was shaken at 37° C. for 30 minutes. After shaking, the beads were washed twice with PBS and used as the saliva-treated HA (S-HA). The beads prepared in the same conditions except that PBS was added in place of the saliva were used as PBS-treated HA (P-HA).

The bacterial suspension (2 mL) was added to S-HA and P-HA and the mixture was shaken at 37° C. for one hour. In addition, the bacterial suspension alone was shaken in the same conditions and used as a control. After completion of the reaction, the test samples were allowed to stand still at room temperature for 10 minutes, and the supernatants (1 mL) were collected in new tubes. In order to dissolve fine HA beads, 0.1 M EDTA (100 µL) was added to the supernatants. After stirring, the test samples were allowed to stand still at room temperature for one hour. Thereafter, absorbance at 550 nm was measured and the ratio of bacterial cells adhered to HA beads was calculated in accordance with the following expression (1) as an adhesion rate (%).

$$\text{Adhesion rate}(\%) = \frac{OD_{Control} - OD_{Sample}}{OD_{Control}} \times 100 \quad (1)$$

The results are shown in Tables 5 and 6. Of the 241 strains selected in Test Examples 2 and 3, 76% of the bacterial strains classified into the genus *Streptococcus* adhered to S-HA. Furthermore, it is generally known that the adhesiveness of lactic acid bacillus to tooth surfaces is low (H. J. Busscher. "In vitro Adhesion to Enamel and in vivo Colonization of Tooth Surfaces by Lactobacilli from a Bio-Yoghurt" Caries Res 1999: 33: 403-404.); however, *Lactobacillus fermentum* and *Lactobacillus gasseri* showed high adhesiveness to S-HA in this order.

TABLE 5

Comparison of rate of adhesion to S-HA between species of isolated bacterial strains (genus *Streptococcus*)

| Bacterial species (number of strains evaluated) | Adhesion rate (%)[a] |
|---|---|
| *Streptococcus salivarius* (38) | 13.7 ± 10.5 |
| *Streptococcus oralis* (26) | 10.3 ± 10.4 |
| *Streptococcus parasanguinis* (20) | 9.0 ± 9.5 |
| *Streptococcus mitis* (21) | 7.2 ± 10.0 |
| *Streptococcus sanguinis* (24) | 5.9 ± 6.5 |
| *Streptococcus* sp. (7) | 3.4 ± 6.0 |
| *Streptococcus cristatus* (5) | 3.4 ± 3.8 |
| *Streptococcus infantis* (2) | 0.4 ± 0.5 |

[a]Average value ± standard deviation

TABLE 6

Comparison of rate of adhesion to S-HA between species of isolated bacterial strains (genus *Lactobacillus*)

| Bacterial species (number of strains evaluated) | Adhesion rate (%)[a] |
|---|---|
| *Lactobacillus fermentum* (16) | 4.9 ± 8.1 |
| *Lactobacillus casei* (5) | 2.4 ± 3.7 |
| *Lactobacillus gasseri* (31) | 1.6 ± 3.5 |
| *Lactobacillus salivarius* (2) | 0.0 |
| *Lactobacillus mucosae* (1) | 0.0 |
| *Lactobacillus crispatus* (5) | N.D |

[a]Average value ± standard deviation
N.D. not determined

Test Example 6

Evaluation of Adhesiveness to Oral Cells

From the 241 strains selected from the results of Test Examples 2 and 3, the bacterial strains, which were determined to have a problem in safety as the results of the identification test, were removed and the remaining strains were used in the following test.

1) Culture of Cell Strains

HO-1-N-1 cells (JCRB0831: cells derived from human buccal mucosa squamous cell carcinoma, hereinafter simply referred to as "HO") and HSC-3 cells (JCRB0623: cells derived from human tongue squamous cell carcinoma, hereinafter simply referred to as "HSC") were cultured at 37° C. in 5.0% $CO_2$. HO cells were cultured in DMEM medium (11885, GIBCO) containing 10% fetal bovine serum; whereas HSC were cultured in DMEM/F12 medium (11320, GIBCO) containing 10% fetal bovine serum.

2) Evaluation of Adhesiveness to Cells

Cells were suspended in a medium containing 10% fetal bovine serum so as to obtain $1.0 \times 10^5$ cells/mL. The suspension was added to the wells in Lab-Tek II chamber slide (Nalge Nunc) (200 µL/well) and cultured for 48 to 96 hours. Thereafter, the cells not adhered to the slide glass surface were removed by washing with RPMI1640. After each of the isolated strains was cultured in MRS liquid medium overnight, a sample containing viable cells of the bacterial strain and satisfying $OD_{660}=0.25$ was prepared and added to the wells (200 µL/well), followed by incubation at 37° C. for 10 minutes. Thereafter, the cells were washed three times with RPMI1640 to remove bacterial cells not adhered to the cells. After the adhesion materials on the slide were subjected to gram staining, the number of bacterial cells adhered to the cells contained in an area of 0.16 mm² was determined by an optical microscope. Note that determination was performed in arbitrary chosen 6 fields of vision.

The results are shown in Tables 7 and 8. It was confirmed that, in 7 strains of the genus *Lactobacillus* and 17 strains of the genus *Streptococcus*, 10 or more bacterial cells adhered to the total of HO cells and HSC cells each contained in an area of 0.16 mm².

It was confirmed that *Lactobacillus crispatus* YIT 12319, *Lactobacillus fermentum* YIT 12320, *Lactobacillus gasseri* YIT 12321, and *Streptococcus mitis* YIT 12322 each have high adhesiveness (i.e., 30 or more bacterial cells/unit area).

TABLE 7

Adhesiveness of isolated bacterial strains (genus *Lactobacillus*) to oral cells

| Bacterial strain No. | | HO-1-N-1 (n = 6) cells/ 0.16 mm² | HSC-3 (n = 6) cells/ 0.16 mm² | Total cells/ 0.16 mm² |
|---|---|---|---|---|
| *Lactobacillus casei* | LBS16-11 | 3.67 | 0.00 | 3.67 |
| *Lactobacillus casei* | LBS16-12 | 0.50 | 5.33 | 5.83 |
| *Lactobacillus casei* | LBS46-32 | 1.17 | 2.50 | 3.67 |
| *Lactobacillus crispatus* | YIT 12319 | 10.67 | 138.33 | 149.00 |
| *Lactobacillus crispatus* | LBS17-11 | 59.33 | 84.17 | 143.50 |
| *Lactobacillus fermentum* | YIT 12320 | 15.00 | 42.50 | 57.50 |
| *Lactobacillus fermentum* | LBS32-12 | 1.83 | 9.67 | 11.50 |
| *Lactobacillus fermentum* | LBS32-11 | 0.00 | 1.67 | 1.67 |
| *Lactobacillus fermentum* | LBS17-32 | 0.33 | 0.33 | 0.67 |
| *Lactobacillus fermentum* | LBS49-31 | 0.17 | 0.00 | 0.17 |
| *Lactobacillus gasseri* | YIT 12321 | 6.67 | 27.17 | 33.83 |
| *Lactobacillus gasseri* | LBS07-11 | 3.33 | 1.17 | 4.50 |
| *Lactobacillus gasseri* | LBS19-11 | 2.33 | 1.00 | 3.33 |

TABLE 7-continued

Adhesiveness of isolated bacterial strains (genus *Lactobacillus*) to oral cells

| Bacterial strain No. | | HO-1-N-1 (n = 6) cells/ 0.16 mm² | HSC-3 (n = 6) cells/ 0.16 mm² | Total cells/ 0.16 mm² |
|---|---|---|---|---|
| Lactobacillus gasseri | LBS22-31 | 4.67 | 1.83 | 6.50 |
| Lactobacillus gasseri | LBS32-41 | 0.00 | 0.00 | 0.00 |
| Lactobacillus gasseri | LBS39-11 | 4.00 | 6.50 | 10.50 |
| Lactobacillus gasseri | LBS43-11 | 0.33 | 0.67 | 1.00 |
| Lactobacillus gasseri | LBS46-21 | 3.33 | 1.67 | 5.00 |
| Lactobacillus mucosae | LBS06-31 | 12.67 | 3.17 | 15.83 |
| Lactobacillus arts | LBS18-13 | 0.00 | 0.00 | 0.00 |
| Lactobacillus salivarius | LBS46-11 | 0.58 | 1.78 | 2.37 |
| Lactobacillus ultunensis | LBS07-21 | 0.67 | 2.83 | 3.50 |

TABLE 8

Adhesiveness of isolated bacterial strains (genus *Streptococcus*) to oral cells

| Bacterial strain No. | | HO-1-N-1 (n = 6) cells/ 0.16 mm² | HSC-3 (n = 6) cells/ 0.16 mm² | Total cells/ 0.16 mm² |
|---|---|---|---|---|
| S. infantis | MRS20-31 | 2.50 | 28.83 | 31.33 |
| S. mitis | MRS08-21 | 1.33 | 0.00 | 1.33 |
| S. mitis | YIT 12322 | 20.50 | 11.67 | 32.17 |
| S. mitis | MRS09-41 | 13.33 | 35.33 | 48.67 |
| S. mitis | MS06-32 | 53.83 | 53.83 | 107.67 |
| S. mitis | MS08-23 | 20.00 | 39.83 | 59.83 |
| S. mitis | MS09-11 | 2.67 | 7.33 | 10.00 |
| S. mitis | MS09-51 | 35.67 | 75.50 | 111.17 |
| S. mitis | MS19-11 | 0.00 | 0.00 | 0.00 |
| S. mitis | MS55-52 | 2.00 | 2.33 | 4.33 |
| S. mitis | MS60-23 | 2.00 | 0.00 | 2.00 |
| S. oralis | MRS19-81 | 14.33 | 27.00 | 41.33 |
| S. oralis | MRS21-13 | 0.17 | 2.17 | 2.33 |
| S. salivarius | MRS09-71 | 57.50 | 53.67 | 111.17 |
| S. salivarius | MRS22-11 | 11.50 | 9.67 | 21.17 |
| S. salivarius | MRS32-81 | 25.00 | 2.00 | 27.00 |
| S. salivarius | MRS49-32 | 38.83 | 17.33 | 56.17 |
| S. salivarius | MS06-12 | 40.67 | 71.33 | 112.00 |
| S. salivarius | MS07-22 | 119.17 | 77.83 | 197.00 |
| S. salivarius | MS08-61 | 1.17 | 0.17 | 1.33 |
| S. salivarius | MS10-11 | 16.50 | 18.33 | 34.83 |
| S. salivarius | MS10-21 | 13.33 | 15.33 | 28.67 |
| S. salivarius | MS16-52 | 0.50 | 1.00 | 1.50 |
| S. salivarius | MRS18-31 | 59.50 | 10.83 | 70.33 |
| S. salivarius | MS20-22 | 0.00 | 3.00 | 3.00 |
| S. salivarius | MS32-81 | 2.83 | 5.00 | 7.83 |

Test Example 7

Evaluation of Growth Inhibition Against Bad Breath-causing Bacteria (Periodontal Pathogens)

From the results of the aforementioned Test Examples, bacterial strains shown in Tables 10 and 11 were selected. As the target bacterial strains, bad breath-causing bacteria and periodontal pathogens, namely, *Porphyromonas gingivalis* ATCC 33277, *Prevotella intermedia* ATCC 25611, and *Aggregatibacter actinomycetemcomitans* Y4; and cariogenic bacteria, namely, *Streptococcus mutans* ATCC 25175 and *Streptococcus sobrinus* ATCC 33478 were used.

One platinum loop of each of the isolated bacterial strains was inoculated in 4.0 mL of MRS liquid medium. After 24 hours culture, the supernatant was obtained by centrifugation (1,912×g, 10 minutes, 4° C.). Furthermore, the supernatant was filtered through a 0.22 μm filter. The resultant filtrate was used as a test sample. The antimicrobial activity of each sample was measured by radial diffusion assay. To 10 mL of TS medium (Tryptic soy broth (Difco) (6.0 mg), Tween 20 (2.0 μL), agarose (100 mg), H₂O (10 mL)), the BHI culture solution (100 μL) of each target bacterial strain was added. The medium mixture was sufficiently stirred and solidified in a Petri dish. After solidification of the medium, a hole of 2.5 mm in diameter was formed and filled with the test sample (5.0 μL). After one hour culture at 37° C., the TS medium (Tryptic soy broth (Difco) (0.6 mg), agarose (100 mg), H₂O (10 mL)) was layered, followed by culture at 37° C. The culture conditions are shown in Table 9. After completion of culture, the diameter of a clear zone region where no bacteria grew (inhibition zone) formed outside the hole was calculated in accordance with the following expression (2) based on measurement.

Inhibition zone diameter (mm)=diameter (mm) of test sample clear zone−diameter of the hole (mm)     (2)

TABLE 9

Culture conditions and positive controls in determining growth inhibitory effect

| Bacterial species | Positive control | Culture time (h) | Culture conditions |
|---|---|---|---|
| S. mutans | Bacitracin 82.5 U/ml | 18 | Anaero Pack anaerobic condition |
| S. sobrinus | Bacitracin 82.5 U/ml | 18 | Anaero Pack anaerobic condition |
| P. gingivalis | Tetracycline•HCl 0.05 mg/ml | 36~48 | Anaerobic box |
| P. intermedia | Tetracycline•HCl 0.2 mg/ml | 36~48 | Anaerobic box |
| A. actinomycetemcomitans | Tetracycline•HCl 0.1 mg/ml | 18~48 | Anaerobic box |

These results are shown in Tables 10 and 11. It was confirmed that, among the isolated bacterial strains, the culture supernatants of the strains of the genus *Lactobacillus* have strong growth inhibitory effect on *Porphyromonas gingivalis*. Furthermore, the growth inhibitory effects on *Prevotella intermedia* and *Aggregatibacter actinomycetemcomitans* were also confirmed. In this test, even though the pH of the culture supernatant was adjusted to 7.0, some of them showed the inhibitory effect on *Porphyromonas gingivalis*. From this, it was considered that there is a high possibility that these strains produce antibiotic substances such as hydrogen peroxide and bacteriocin other than organic acids. Furthermore, it was confirmed that *Lactobacillus crispatus* YIT 12319 has a growth inhibitory effect on cariogenic bacteria, namely *Streptococcus mutans* and *Streptococcus sobrinus*. As a result of a test performed by adjusting the pH of the culture supernatant to 7.0, no growth inhibitory effect of this strain was confirmed; however, since *Streptococcus mutans* and *Streptococcus sobrinus* produce an acid and thus the bacteria themselves are acid resistance, the possibility that growth is suppressed by pH reduction is conceivably low. Therefore, it was considered that *Lactobacillus crispatus* YIT 12319 may possibly produce antibiotic substances such as hydrogen peroxide and bacteriocin.

Also among the strains of the genus *Streptococcus*, it was confirmed that the culture supernatants of 15 strains have growth inhibitory effect on bad breath-causing bacteria (periodontal pathogens); however, the effect was low compared to the isolated strains of the genus *Lactobacillus*. Even if the pH of the supernatant was adjusted to 7.0, these strains were able to inhibit the growth of *Porphyromonas gingivalis*. From this, it was considered that these strains may possibly produce antibiotic substances such as hydrogen peroxide and bacteriocin, similarly to the case of isolated bacterial strains of the genus *Lactobacillus*.

Each of *Lactobacillus crispatus* YIT 12319, *Lactobacillus fermentum* YIT 12320, *Lactobacillus gasseri* YIT 12321, and *Streptococcus mitis* YIT 12322 was confirmed to have a strong growth inhibitory effect indicated by the sum of diameters of inhibition zones being 9 mm or more.

TABLE 10

Growth inhibitory effect of isolated bacterial strains (genus *Lactobacillus*) on bad breath-causing bacteria (periodontal pathogens) and cariogenic bacteria

| | | Inhibition zone diameter (mm) for each bacterial strain* | | | | | | | | | Sum of inhibition zone diameters |
|---|---|---|---|---|---|---|---|---|---|---|---|
| | | Ss | | Sm | | Pg | | Pi | | Aa | |
| Bacterial strain No. | | (−) | (+) | (−) | (+) | (−) | (+) | (−) | (+) | (−) | (+) | (mm) |
| *L. casei* | LBS16-11 | 0.00 | 0.00 | 0.00 | 0.00 | 5.69 | 0.00 | 5.20 | 0.00 | 3.64 | 0.00 | 14.53 |
| *L. casei* | LBS16-12 | 0.00 | 0.00 | 0.00 | 0.00 | 5.51 | 0.00 | 5.65 | 0.00 | 4.01 | 0.00 | 15.17 |
| *L. casei* | LBS46-32 | 0.00 | 0.00 | 0.00 | 0.00 | 4.91 | 0.00 | 3.29 | 0.00 | 2.92 | 0.00 | 11.12 |
| *L. crispatus* | YIT 12319 | 0.81 | 0.00 | 0.32 | 0.00 | 4.72 | 6.12 | 5.18 | 0.00 | 1.99 | 2.96 | 22.10 |
| *L. crispatus* | LBS17-11 | 0.00 | 0.00 | 0.00 | 0.00 | 5.46 | 0.00 | 5.01 | 0.00 | 3.39 | 0.00 | 13.86 |
| *L. fermentum* | YIT 12320 | 0.00 | 0.00 | 0.00 | 0.00 | 5.38 | 2.56 | 4.45 | 0.00 | 4.45 | 0.00 | 16.84 |
| *L. fermentum* | LBS32-12 | 0.00 | 0.00 | 0.00 | 0.00 | 4.61 | 0.00 | 2.95 | 0.00 | 3.24 | 0.00 | 10.79 |
| *L. fermentum* | LBS32-11 | 12.3 | 0.00 | 0.00 | 0.00 | 5.35 | 2.25 | 0.00 | 0.00 | 2.61 | 0.00 | 22.46 |
| *L. fermentum* | LBS17-32 | 12.1 | 0.00 | 0.00 | 0.00 | 5.29 | 0.00 | 0.00 | 0.00 | 1.96 | 0.00 | 19.30 |
| *L. fermentum* | LBS49-31 | 0.00 | 0.00 | 0.00 | 0.00 | 5.04 | 1.79 | 4.15 | 0.00 | 3.47 | 0.00 | 14.44 |
| *L. gasseri* | YIT 12321 | 0.00 | 0.00 | 0.00 | 0.00 | 3.45 | 3.61 | 2.24 | 0.00 | 0.00 | 0.00 | 9.30 |
| *L. gasseri* | LBS07-11 | 0.00 | 0.00 | 0.00 | 0.00 | 5.41 | 2.55 | 5.18 | 0.00 | 4.14 | 0.00 | 17.28 |
| *L. gasseri* | LBS19-11 | 0.58 | 0.00 | 2.99 | 0.00 | 6.16 | 7.05 | 2.63 | 0.00 | 3.36 | 0.00 | 22.78 |
| *L. gasseri* | LBS22-31 | 0.00 | 0.00 | 0.00 | 0.00 | 5.93 | 3.00 | 4.11 | 0.00 | 3.41 | 0.00 | 16.45 |
| *L. gasseri* | LBS32-41 | 4.29 | 0.00 | 0.00 | 0.00 | 6.02 | 1.26 | 2.32 | 0.00 | 2.59 | 0.00 | 16.47 |
| *L. gasseri* | LBS39-11 | 0.00 | 0.00 | 0.00 | 0.00 | 3.67 | 5.78 | 0.00 | 0.00 | 1.55 | 0.00 | 11.00 |
| *L. gasseri* | LBS43-11 | 5.47 | 0.00 | 3.50 | 0.00 | 5.31 | 6.69 | 2.42 | 0.00 | 2.96 | 0.00 | 26.34 |
| *L. gasseri* | LBS46-21 | 0.00 | 0.00 | 0.00 | 0.00 | 5.83 | 3.08 | 4.72 | 0.00 | 3.72 | 0.00 | 17.35 |
| *L. mucosae* | LBS06-31 | 0.00 | 0.00 | 0.00 | 0.00 | 5.25 | 1.36 | 3.66 | 0.00 | 3.17 | 0.00 | 13.44 |
| *L. oris* | LBS18-13 | 0.00 | 0.00 | 2.60 | 0.00 | 5.95 | 3.42 | 4.39 | 0.00 | 4.16 | 0.00 | 20.51 |
| *L. salivarius* | LBS46-11 | 9.34 | 0.00 | 3.25 | 0.00 | 5.49 | 6.77 | 2.08 | 0.00 | 3.35 | 0.00 | 30.29 |
| *L. ultunensis* | LBS07-21 | 0.00 | 0.00 | 0.00 | 0.00 | 4.77 | 3.48 | 4.46 | 0.00 | 3.45 | 0.00 | 16.16 |

*Ss; *S. sobrinus* ATCC33478, Sm; *S. mutans* ATCC 25175, Pg; *P gingivalis* ATCC 33277, Pi; *P intermedia* ATCC25611, Aa; *Aggregatibacter actinomycetemcomitans* Y4,
(−); pH of culture supernatant was not adjusted.
(+); pH of culture supernatant was adjusted to 7.0.

TABLE 11

Growth inhibitory effect of isolated bacterial strains (genus *Streptococcus*) on bad breath-causing bacteria (periodontal pathogens) and cariogenic bacteria

| | | Inhibition zone diameter (mm) for each bacteria strain* | | | | | | | | | Sum of inhibition zone diameters |
|---|---|---|---|---|---|---|---|---|---|---|---|
| | | Ss | | Sm | | Pg | | Pi | | Aa | |
| Bacterial strain No. | | (−) | (+) | (−) | (+) | (−) | (+) | (−) | (+) | (−) | (+) | (mm) |
| *S. infantis* | MRS20-31 | 0.00 | 0.00 | 0.00 | 0.00 | 3.37 | 5.64 | 3.68 | 0.00 | 0.00 | 2.73 | 15.42 |
| *S. mitis* | MRS08-21 | 0.00 | 0.00 | 0.00 | 0.00 | 4.02 | 5.91 | 4.34 | 0.00 | 0.79 | 2.37 | 17.43 |
| *S. mitis* | YIT 12322 | 0.00 | 0.00 | 0.00 | 0.00 | 3.21 | 4.60 | 4.46 | 0.00 | 0.00 | 0.00 | 12.27 |
| *S. mitis* | MRS09-41 | 0.00 | 0.00 | 0.00 | 0.00 | 3.41 | 5.01 | 3.74 | 0.00 | 0.00 | 0.00 | 12.16 |
| *S. mitis* | MS06-32 | 0.00 | 0.00 | 0.00 | 0.00 | 3.79 | 0.00 | 4.07 | 0.00 | 0.00 | 0.00 | 7.86 |
| *S. mitis* | MS08-23 | 0.00 | 0.00 | 0.00 | 0.00 | 4.31 | 0.00 | 4.3 | 0.00 | 0.00 | 0.00 | 8.61 |
| *S. mitis* | MS09-11 | 0.00 | 0.00 | 0.00 | 0.00 | 4.03 | 0.00 | 3.1 | 0.00 | 0.00 | 0.00 | 7.13 |
| *S. mitis* | MS09-51 | 0.00 | 0.00 | 0.00 | 0.00 | 3.55 | 0.00 | 0 | 0.00 | 0.00 | 0.00 | 3.55 |
| *S. mitis* | MS19-11 | 0.00 | 0.00 | 0.00 | 0.00 | 4.92 | 0.00 | 2.67 | 0.00 | 0.00 | 0.00 | 7.59 |
| *S. mitis* | MS55-52 | 0.00 | 0.00 | 0.00 | 0.00 | 3.79 | 0.00 | 3.55 | 0.00 | 0.00 | 0.00 | 7.34 |
| *S. mitis* | MS60-23 | 0.00 | 0.00 | 0.00 | 0.00 | 4.31 | 0.00 | 0 | 0.00 | 0.00 | 0.00 | 4.31 |
| *S. oralis* | MRS19-81 | 0.00 | 0.00 | 0.00 | 0.00 | 3.67 | 5.55 | 4.13 | 0.00 | 0.57 | 2.83 | 16.75 |
| *S. oralis* | MRS21-13 | 0.00 | 0.00 | 0.00 | 0.00 | 4.02 | 4.51 | 4.42 | 0.00 | 0.79 | 0.00 | 13.74 |
| *S. salivarius* | MRS09-71 | 0.00 | 0.00 | 0.00 | 0.00 | 3.08 | 5.75 | 4.26 | 0.00 | 0.00 | 1.66 | 14.75 |
| *S. salivarius* | MRS22-11 | 0.00 | 0.00 | 0.00 | 0.00 | 3.71 | 5.09 | 4.54 | 0.00 | 2.20 | 3.28 | 18.82 |
| *S. salivarius* | MRS32-81 | 0.00 | 0.00 | 0.00 | 0.00 | 3.08 | 4.36 | 4.68 | 0.00 | 0.00 | 2.34 | 14.45 |
| *S. salivarius* | MRS49-32 | 0.00 | 0.00 | 0.00 | 0.00 | 2.99 | 6.71 | 0.00 | 0.00 | 1.06 | 0.00 | 10.76 |
| *S. salivarius* | MS06-12 | 0.00 | 0.00 | 0.00 | 4.29 | 0.00 | 3.43 | 0.00 | 0.00 | 0.00 | 0.00 | 7.72 |
| *S. salivarius* | MS07-22 | 0.00 | 0.00 | 0.00 | 0.00 | 5.79 | 0.00 | 3.24 | 0.00 | 0.00 | 0.00 | 9.03 |
| *S. salivarius* | MS08-61 | 0.00 | 0.00 | 0.00 | 5.47 | 0.00 | 4.35 | 0.00 | 0.00 | 0.00 | 0.00 | 9.82 |
| *S. salivarius* | MS10-11 | 0.00 | 0.00 | 0.00 | 4.90 | 0.00 | 0 | 0.00 | 0.00 | 0.00 | 0.00 | 4.90 |
| *S. salivarius* | MS10-21 | 0.00 | 0.00 | 0.00 | 5.69 | 0.00 | 3.64 | 0.00 | 0.00 | 0.00 | 0.00 | 9.33 |
| *S. salivarius* | MS16-52 | 0.00 | 0.00 | 0.00 | 0.00 | 4.47 | 0.00 | 3.77 | 0.00 | 0.00 | 0.00 | 8.24 |
| *S. salivarius* | MRS18-31 | 0.00 | 0.00 | 0.00 | 0.00 | 4.32 | 6.38 | 4.86 | 0.00 | 1.87 | 2.55 | 19.99 |

TABLE 11-continued

Growth inhibitory effect of isolated bacterial strains (genus *Streptococcus*) on bad breath-causing bacteria (periodontal pathogens) and cariogenic bacteria

|  | | Inhibition zone diameter (mm) for each bacteria strain* | | | | | | | | | Sum of inhibition zone diameters (mm) |
|---|---|---|---|---|---|---|---|---|---|---|---|
|  | | Ss | | Sm | | Pg | | Pi | | Aa | |
| Bacterial strain No. | | (−) | (+) | (−) | (+) | (−) | (+) | (−) | (+) | (−) | (+) | |
| *S. salivarius* | MS20-22 | 2.75 | 0.00 | 2.82 | 0.00 | 5.81 | 0.00 | 3.52 | 0.00 | 0.00 | 0.00 | 14.90 |
| *S. salivarius* | MS32-81 | 0.00 | 0.00 | 0.00 | 5.20 | 0.00 | 2.67 | 0.00 | 0.00 | 0.00 | 0.00 | 7.87 |

*Ss; *S. sobrinus* ATCC33478, Sm; *S. mutans* ATCC 25175, Pg; *P gingivalis* ATCC 33277, Pi; *P intermedia* ATCC25611, Aa; *Aggregatibacter actinomycetemcomitans*Y4,
(−); pH of culture supernatant was not adjusted.
(+); pH of culture supernatant was adjusted to 7.0.

Test Example 8

Evaluation of Causative Role in Infective Endocarditis Using Rat Experimental Endocarditis Model From the results of the aforementioned Test Examples, bacterial strains shown in Tables 12 and 13 were selected. As a positive control, an endocarditis causing bacterium, namely, *Lactobacillus rhamnosus* YIT 0227, was used.

As test animals, 102 Crl:CD (SD) male rats of 8 weeks after birth (Charles River Laboratories Japan Inc.) were used.

Experimental endocarditis (non-bacterial endocarditis) model animals were prepared as follows. As an anesthetic, a mixture of Ketalar (containing 50 mg/mL ketamine hydrochloride) and Selactar (containing 20 mg/mL xylazine hydrochloride) in a ratio of 18:5 was prepared. Then, the anesthetic was intraperitoneally administered in a dose of 2 mL/kg. Thereafter, the cervical skin was excised under anesthesia to expose the right carotid artery and a catheter of about 20 cm using a polyethylene tube (SP10, Natsume Seisakusho Co. Ltd.) of 0.61 mm in outer diameter was inserted from the right carotid artery to the left ventricle and allowed to indwell there. On the next day of the day when the non-bacterial thrombotic endocarditis animals were prepared, a bacterial suspension was administered into the caudal vein by use of a disposable syringe (1 mL) and an injection needle 27G so as to provide 0.5 mL/rat.

The bacterial suspension administered was prepared as follows. First, to MRS medium (4 mL), an isolated strain (10 µL) was inoculated and cultured at 37° C. for 20 hours. The culture solution (100 µL) was inoculated to fresh MRS medium (10 mL) and further cultured at 37° C. for 20 hours. After completion of culture, the culture solution was centrifuged (1,670×g, 10 minutes, 4.0° C.) to remove the supernatant. An equal amount of physiological saline to that of the medium was added thereto and the mixture was sufficiently stirred by a vortex to wash and again centrifuged (1,670×g, 10 minutes, 4.0° C.) to remove the supernatant. After this washing operation was repeated three times, the collected bacterial cells were diluted with physiological saline so as to obtain a standard bacterial count (4.0 to 9.0×10$^6$ CFU/mL). In this manner, the bacterial suspension to be administered was obtained.

Four days after administration date of a test bacterial strain, the peripheral venous blood was sampled and serially diluted with physiological saline. Each of the undiluted solution (0.5 mL) and a 10$^{-2}$ dilution solution (1.0 mL) was plated on MRS plate medium by a pour method. After culture at 37° C. for 3 days, the number of colonies grown on the plates was counted to calculate the number of viable bacterial cells in 1 mL of blood. Similarly, a homogenate solution of a heart containing wart was serially diluted with physiological saline. Each of the undiluted solution, 10$^{-2}$, 10$^{-4}$, and 10$^{-6}$ dilution solutions (1.0 mL) was plated on MRS plate medium by a pour method. After culture at 37° C. for 3 days, the number of colonies grown on the plates was counted to calculate the number of viable bacterial cells. Note that in the case where no colonies were detected in both of two plates, assuming that a single colony was detected in either one of the plates, the numerical value obtained by dividing 1 by the weight of wart was regarded as a detection limit value.

The results are shown in Tables 12 and 13. In the rats to which a positive control, YIT 0227, was administered, administered viable cells were detected in 5 out of 6 blood samples (1 to 28 CFU/mL) and in all specimens of wart (1.4×10$^3$ to 1.7×10$^6$ CFU/heart). In contrast, in the rats to which *Lactobacillus crispatus* YIT 12319, *Lactobacillus crispatus* LBS 17-11, *Lactobacillus fermentum* YIT 12320, and *Lactobacillus gasseri* YIT 12321 were administered, no administered viable cells were detected in blood and wart. Accordingly, it was determined that endocarditis causative role of these bacterial strains were negative in rats.

Furthermore, in the rats to which *Streptococcus mitis* YIT 12322 was administered, administered viable cells were not detected in blood and detected in wart from a single specimen. The endocarditis causative role of the bacterial strain was determined as being negative. In the rats to which other bacterial strains were administered, the administered bacteria were detected in the wart from all individuals and the numbers of detected cells were high (6.2×10$^4$ to 9.4×10$^6$ CFU/heart). Therefore, these strains were determined as being positive.

TABLE 12

Test for infective endocarditis causative role of isolated
bacterial strains (genus *Lactobacillus*) using rat models

| Bacterial strain No. | No. of bacteria detected/viable | | CFU[a] | | Endocarditis causative role in rats |
|---|---|---|---|---|---|
| | Blood | Wart | Blood (/ml) | Wart (/g) | |
| *L. fermentum* YIT 12320 | 0/6 (0%) | 0/6 (0%) | 0 | <3.5[b] | Negative |
| *L. crispatus* LBS 17-11 | 0/5 (0%) | 0/5 (0%) | 0 | <3.5[b] | Negative |
| *L. crispatus* YIT 12319 | 0/4 (0%) | 0/4 (0%) | 0 | <3.5[b] | Negative |
| *L. gasseri* YIT 12321 | 0/6 (0%) | 0/6 (0%) | 0 | <3.5[b] | Negative |
| *L. rhamnosus* YIT 0227 | 5/6 (83%) | 6/6 (100%) | 8.4 | $4.7 \times 10^4$ | Positive |

[a]Average bacterial count in bacteria-detected individuals
[b]Detection limit value or less

TABLE 13

Test for infective endocarditis causative role of isolated bacterial strains (genus
*Streptococcus*) using rat models

| Bacterial strain No. | | No. of bacteria detected/viable | | CPU[a] | | Endocarditis causative role in rats |
|---|---|---|---|---|---|---|
| | | Blood | Wart | Blood (/ml) | Wart (/g) | |
| *S. infantis* | MRS20-31 | 1/3 (33%) | 6/7 (86%) | $3.3 \times 10^1$ | $4.7 \times 10^5$ | Positive |
| *S. mitis* | MRS08-21 | 3/6 (50%) | 6/6 (100%) | 9.3 | $2.7 \times 10^6$ | Positive |
| *S. mitis* | YIT 12322 | 0/5 (0%) | 1/5 (20%) | 0 | $8.5 \times 10^2$ | Negative |
| *S. mitis* | MRS09-41 | 5/5 (100%) | 5/5 (100%) | $7.0 \times 10^1$ | $1.2 \times 10^6$ | Positive |
| *S. oralis* | MRS19-81 | 0/5 (0%) | 5/5 (100%) | 0 | $2.9 \times 10^5$ | Positive |
| *S. salivarius* | MRS09-71 | 5/5 (100%) | 5/5 (100%) | $7.0 \times 10^2$ | $1.2 \times 10^6$ | Positive |
| *S. salivarius* | MRS49-32 | 2/2 (100%) | 2/2 (100%) | $2.6 \times 10^3$ | $3.7 \times 10^6$ | Positive |
| *S. salivarius* | MS07-22 | 1/1 (100%) | 7/7 (100%) | $1.5 \times 10^3$ | $8.4 \times 10^6$ | Positive |
| *S. salivarius* | MS10-11 | 3/3 (100%) | 3/3 (100%) | $7.9 \times 10^2$ | $1.8 \times 10^6$ | Positive |
| *S. salivarius* | MRS18-31 | 5/5 (100%) | 5/5 (100%) | $1.5 \times 10^2$ | $6.2 \times 10^4$ | Positive |

[a]Average bacterial count in bacteria-detected individuals

Test Example 9

Evaluation of Cariogenicity by Use of an Artificial Oral Cavity System

*Lactobacillus crispatus* YIT 12319, *Lactobacillus fermentum* YIT 12320, *Lactobacillus gasseri* YIT 12321, *Streptococcus mitis* YIT 12322, *Lactobacillus crispatus* LBS 17-11, and *Lactobacillus gasseri* LBS 46-52 were used. As a positive control, *Streptococcus sobrinus* 6715 and *Streptococcus sobrinus* ATCC 33478 were used.

From each of the test tubes storing isolated bacterial strains, three platinum loops of the bacterial strain was inoculated in a test tube containing fresh TS medium or MRS medium (4 mL) and anaerobically cultured at 37° C. for 16 hours. The culture solution (4 mL) was inoculated in fresh TS or MRS medium (1 L) and anaerobically cultured at 37° C. for 16 hours. The culture solution was centrifuged (4,830×g, 20 minutes, 4° C.) to collect bacterial cells. The bacterial cells were washed with PBS, further centrifuged and then suspended in 200 mL of PBS. An aliquot was taken from the suspension and diluted (1/10) with PBS. The turbidity thereof was then measured at 540 nm. The turbidity of the whole suspension was adjusted with PBS so as to obtain OD540=0.5 or 1.0.

A change in hardness of bovine dental enamel with the bacterial suspension was measured by an artificial oral cavity system. More specifically, a change in pH with time was measured by a pH meter set under an artificial biofilm. Furthermore, a change in hardness of bovine dental enamel was obtained based on a change in Vickers hardness of a tooth piece before and after the experiment. Furthermore, each of bovine dental enamel pieces was soaked in 0.5 N NaOH (2 mL) at 0° C. for 10 minutes to release an artificial biofilm and then centrifuged (4,830×g, 20 minutes) to fractionate the bacterial cells and the supernatant (water-insoluble glucan fraction). The bacterial cells were suspended in PBS and the turbidity at OD540 nm was measured. From the turbidity measured, the amount of bacterial cells per tooth piece (mm²) was obtained. Furthermore, the amount of water-insoluble glucan in the supernatant was measured by the phenol sulfate method.

Note that *Lactobacillus gasseri* YIT 12321 was evaluated for cariogenicity by the artificial oral cavity system in the conditions where the bacterial cell concentration and reaction time were both doubled.

Figure 2:
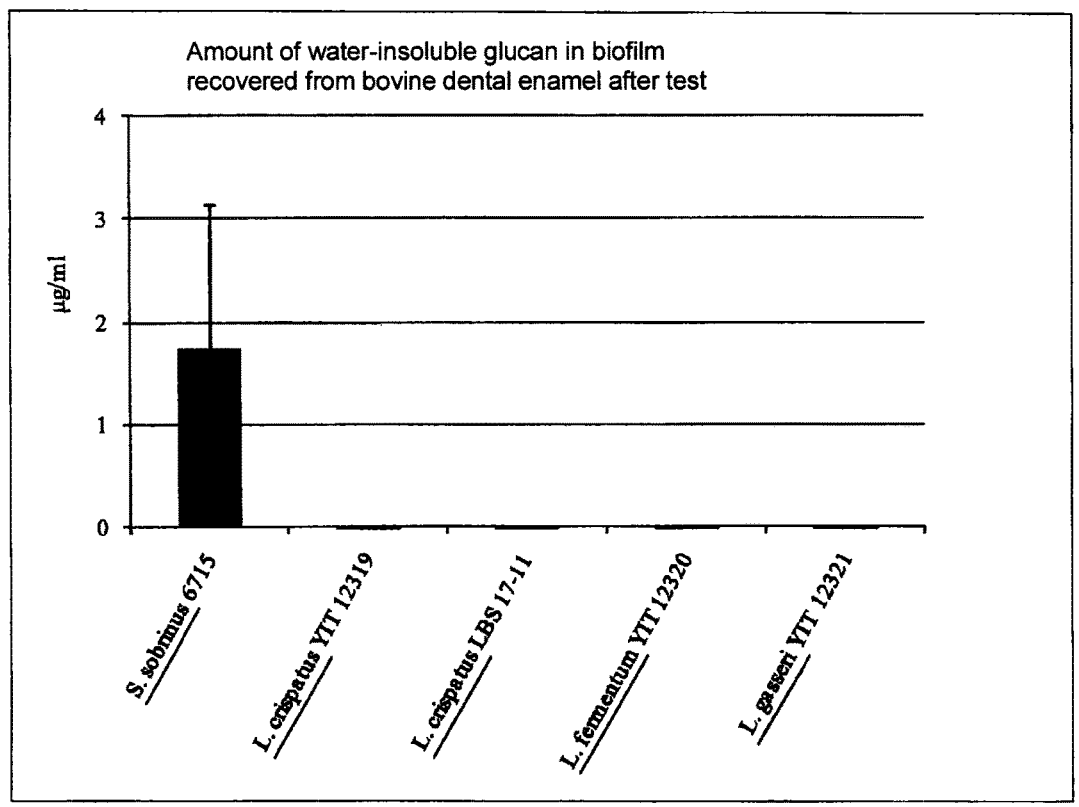
FIG. 2 is a graph showing the amount of water-insoluble glucan in a biofilm collected from the bovine dental enamel which was exposed with YIT 12319 to 12321.
Figure 3:
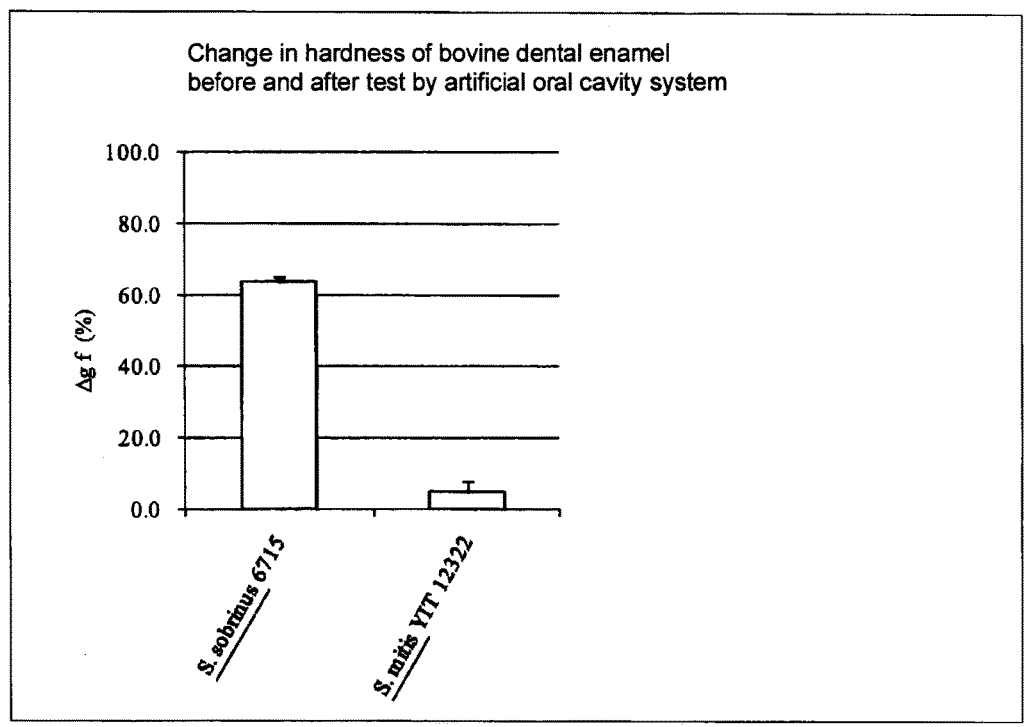
FIG. 3 is a graph showing the change in the hardness of bovine dental enamel which was exposed with YIT 12322.

The results are shown in FIGS. 1 to 4. In the case of cariogenic bacterium, namely, *Streptococcus sobrinus* 6715, the hardness of bovine dental enamel in contact with this bacterium in the presence of sucrose for 20 hours decreased by about 60 to 80% compared to that before initiation of the test (FIGS. 1 and 3). Furthermore, since water-insoluble glucan and bacterial cells were recovered from the dental enamel (FIG. 2), it was presumed that the bacterium forms a biofilm mainly consisting of water-insoluble glucan on the surface of the dental enamel and produces an acid in the film, thereby facilitating decalcification, with the result that the hardness reduces.

Figure 4:
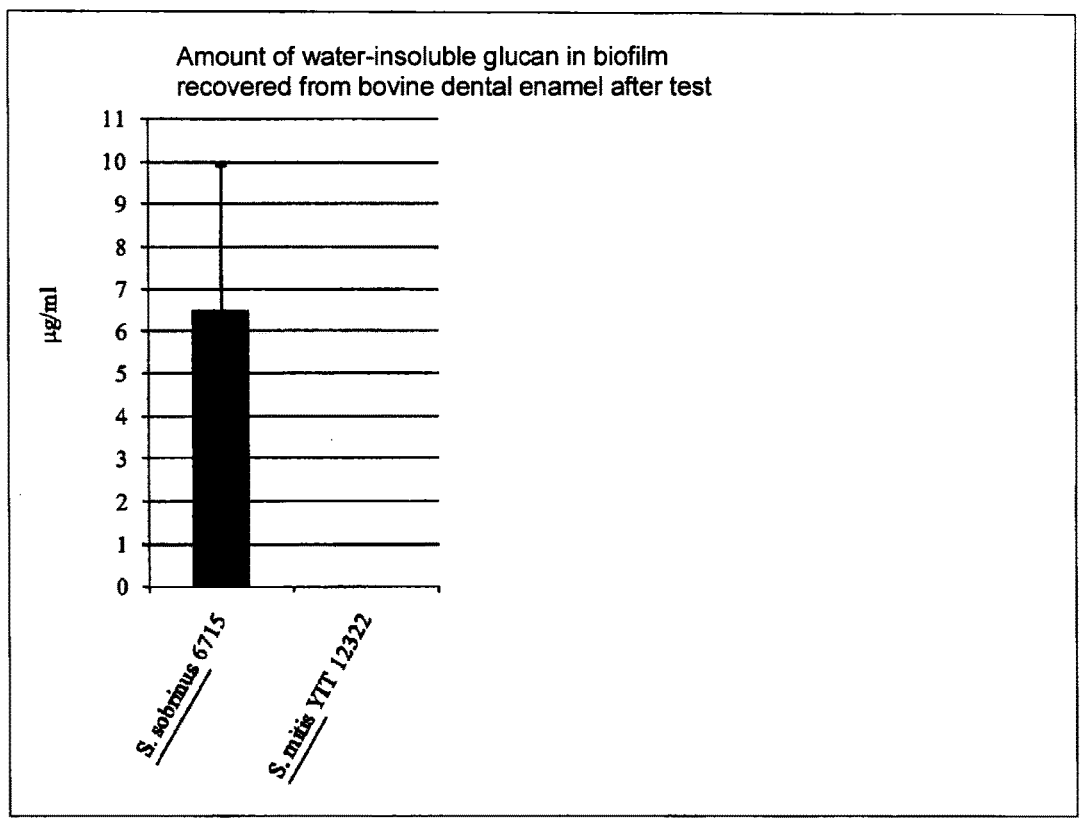
FIG. 4 is a graph showing the amount of water-insoluble glucan in the biofilm collected from the bovine dental enamel which was exposed with YIT 12322.

In contrast, the reduction rates of hardness in the cases of *Lactobacillus crispatus* YIT 12319, *Lactobacillus fermentum* YIT 12320, *Lactobacillus gasseri* YIT 12321, and *Streptococcus mitis* YIT 12322 were each less than 5% (FIGS. 1 and 3). Furthermore, water-insoluble glucan was not recovered from any one of dental enamels to which the bacterial strains were applied (FIGS. 2 and 4).

Figure 5:
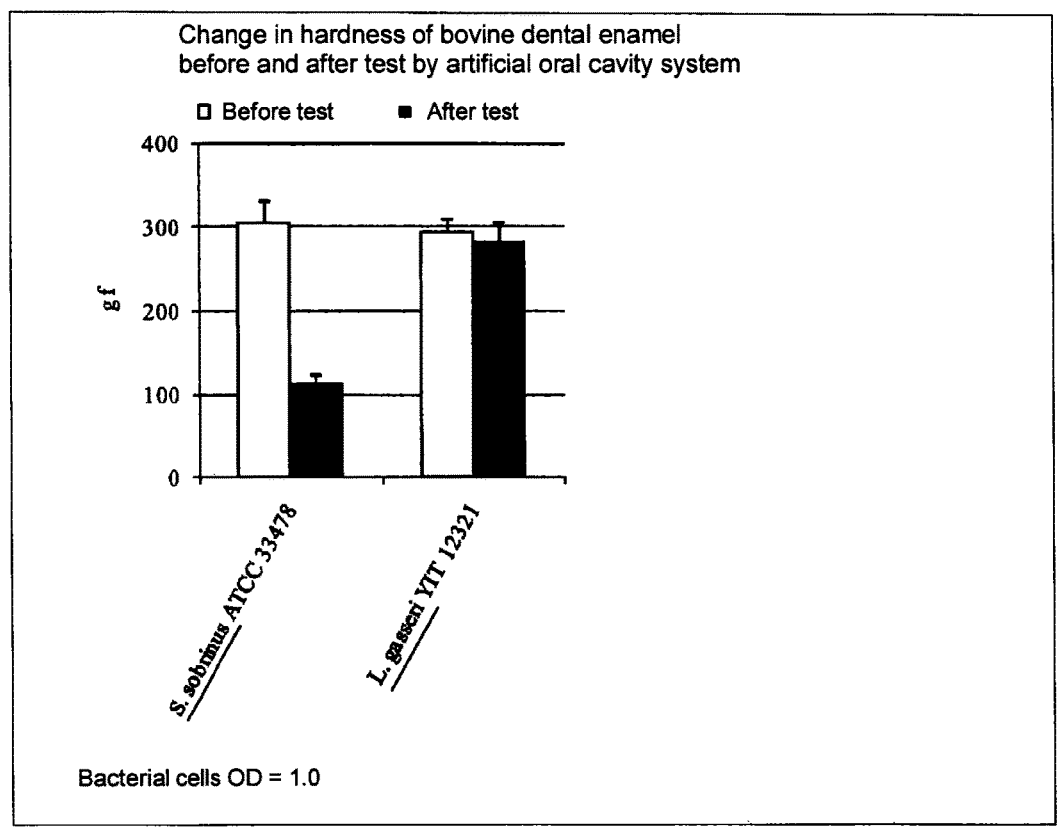
FIG. 5 is a graph showing the change in hardness of the bovine dental enamel which was exposed with YIT 12321.

The cariogenicity of *Lactobacillus gasseri* YIT 12321 was checked by an artificial oral cavity system in the conditions where bacterial cell concentration and reaction time were both doubled. The results are shown in FIG. 5. The reduction rate of dental enamel hardness was 4.4%, which is almost same as in the original conditions. From this, it was considered that even if this bacterium is excessively taken, the possibility of causing caries is low.

To investigate why the hardness of bovine dental enamel does not decrease, ability of *Lactobacillus gasseri* YIT 12321 to utilize sucrose was checked. The ability to utilize sucrose was checked by culturing the bacterium in the same medium as ILS liquid medium (BBL Trypticase Peptone (BD) 10 g, yeast extract (BD) 5 g, Bacto Tryptose (BD) 3 g, $KH_2PO_4$ (3 g), $K_2HPO_4$ (3 g), $(NH_4)_3C_6H_5O_7$ (2 g), lactose (20 g), L-cysteine/HCl (0.2 g), $CH_3COONa$ (1 g), Tween 80 (1 g), salt solution ($MgSO_4.7H_2O$ (11.5 g/100 mL), $FeSO_4.7H_2O$ (0.68 g/100 mL), $MnSO_4.5H_2O$ (2.4 g/100 mL)) 5 mL, DW 1000 mL) modified that sucrose was used in place of lactose, at 37° C. for 24 hours. Growth of the bacterium was represented by absorbance (OD) of the culture solution at 660 nm.

Figure 6:
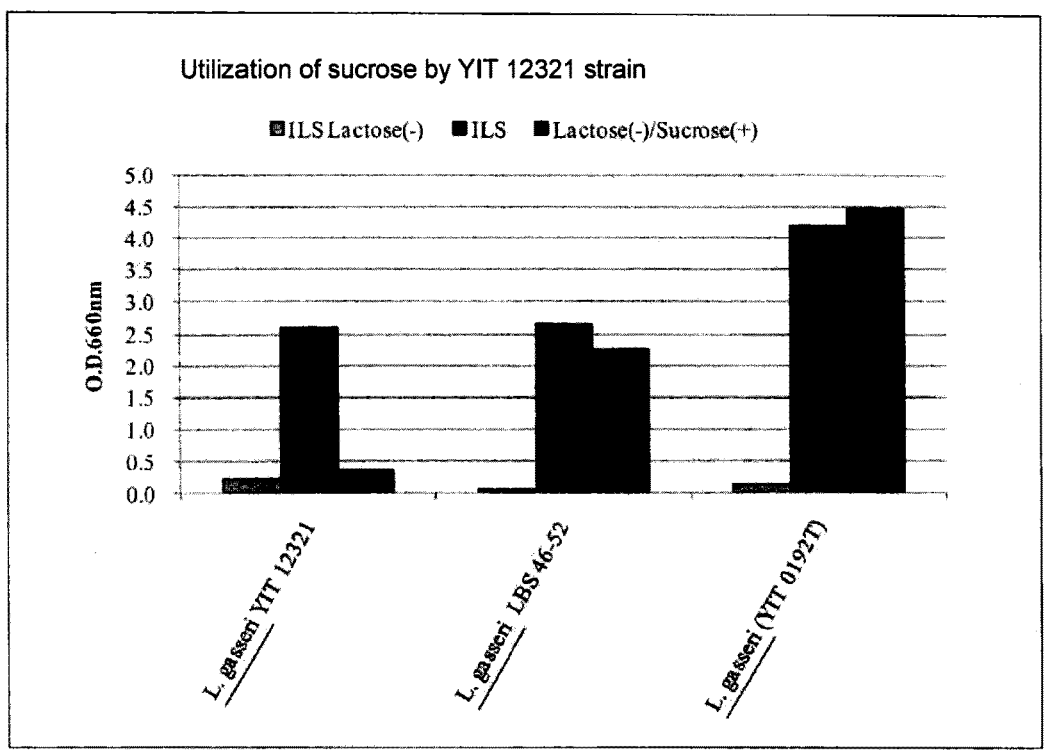
FIG. 6 is a graph showing sucrose utilization by YIT 12321.

As a result, it was elucidated that *Lactobacillus gasseri* YIT 12321 cannot utilize sucrose as a substrate for growth (FIG. 6). Since the type-strain (YIT 0192T) of *Lactobacillus gasseri* can utilize sucrose, it was considered that this property is specific to this strain.

From the results described above, it was considered that bacterial strains, i.e., *Lactobacillus crispatus* YIT 12319, *Lactobacillus fermentum* YIT 12320, *Lactobacillus gasseri* YIT 12321, and *Streptococcus mitis* YIT 12322 separated and tested herein would not be a cause of caries. Particularly YIT 12321, since it does not utilize sucrose, was considered to be more useful.

These strains, namely, YIT 12319, YIT 12320, YIT 12321, and YIT 12322, are novel bacterial strains, which were deposited at the International Patent Organism Depository, Incorporated Administrative Agency National Institute of Technology and Evaluation (address: Central 6, 1-1-1 Higashi, Tsukuba, Ibaraki, Japan) under the names of *Lactobacillus crispatus* YIT 12319 (FERM BP-11500), *Lactobacillus fermentum* YIT 12320 (FERM BP-11501), *Lactobacillus gasseri* YIT 12321 (FERM BP-11502), and *Streptococcus mitis* YIT 12322 (FERM BP-11503).

Regarding bacterial strains having satisfactory results (bacterial strains having none of VSC production ability and water-insoluble glucan production ability and having adhesiveness to tooth surfaces) in Test Examples 2, 3 and 5 as mentioned above, the results of Test Examples 6 to 9 are collectively shown in Table 14. As the results of intensive studies conducted by the present inventors on about 1600 bacterial strains, which were separated from an oral cavity, lactic acid bacteria having all properties of (1) to (6) according to the present invention were found but only 4 strains. It was confirmed that lactic acid bacteria having such specific properties are extremely useful as e.g., foods and drinks and oral compositions for preventing or improving various oral diseases or discomforts.

TABLE 14

| Bacterial species | Bacterial strain | (1) Adhesiveness | (2) Growth inhibition | (3) Causative role | (4) Change in hardness |
|---|---|---|---|---|---|
| *Lactobacillus casei* | LBS16-11 | B | A | | |
| | LBS16-12 | B | A | | |
| | LBS46-32 | B | A | | |
| *Lactobacillus crispatus* | YIT12319 | A | A | A | A |
| | LBS17-11 | A | A | A | B |
| *Lactobacillus fermentum* | YIT12320 | A | A | A | A |
| | LBS32-12 | B | A | | |
| | LBS32-11 | B | A | | |
| | LBS17-32 | B | A | | |
| | LBS49-31 | B | A | | |
| *Lactobacillus gasseri* | YIT12321 | A | A | A | A |
| | LBS07-11 | B | A | | |
| | LBS19-11 | B | A | | |
| | LBS22-31 | B | A | | |
| | LBS32-41 | B | A | | |
| | LBS39-11 | B | A | | |
| | LBS43-11 | B | A | | |
| | LBS46-21 | B | A | | |
| *Lactobacillus mucosae* | LBS06-31 | B | A | | |
| *Lactobacillus oris* | LBS18-13 | B | A | | |
| *Lactobacillus salivarius* | LBS46-11 | B | A | | |
| *Lactobacillus ultunensis* | LBS07-21 | B | A | | |
| *Lactobacillus infalntis* | MRS20-31 | A | A | B | |
| *Streptococcus mitis* | MRS08-21 | B | A | | |
| | YIT12322 | A | A | A | A |
| | MRS09-41 | A | A | B | |
| | MS06-32 | A | B | | |
| | MS08-23 | A | B | | |
| | MS09-11 | B | B | | |
| | MS09-51 | A | B | | |
| | MS19-11 | B | B | | |
| | MS55-52 | B | B | | |
| | MS60-23 | B | B | | |
| *Streptococcus oralis* | MRS19-81 | A | A | B | |
| | MRS21-13 | B | A | | |
| *Streptococcus salivarius* | MRS09-71 | A | A | B | |
| | MRS22-11 | B | A | | |
| | MRS32-81 | B | A | | |
| | MRS49-32 | A | A | B | |
| | MS06-12 | A | B | | |
| | MS07-22 | A | A | B | |
| | MS08-61 | B | A | | |
| | MS10-11 | A | B | B | |
| | MS10-21 | B | A | | |
| | MS16-52 | B | B | | |
| | MRS18-31 | A | A | B | |
| | MS20-22 | B | A | | |
| | MS32-81 | B | B | | |

(1) Adhesiveness: results of Test Example 6 (total cells/0.16 $mm^2$), A: 30 or more, B: less than 30
(2) Growth inhibition: results of Test Example 7 (sum of inhibition zone diameters), A: 9 mm or more, B: less than 9 mm
(3) Causative role: results of Test Example 8 (causative role in infective endocarditis), A: negative, B: positive
(4) Change in hardness: results of Test Example 9 (change in hardness of bovine dental enamel), A: less than 5%, B: 5% or more Test Example 10

Verification of Effect for Improving the Oral Environment in Human

To investigate the effect of intake of the lactic acid bacterium, *Lactobacillus crispatus* YIT 12319, according to the present invention on an oral environment, a test food containing viable bacterial cells ($3.3 \times 10^8$ cfu or more/grain) was continuously given to 17 test subjects having bad breath once a day in a dose of 3 grains per time for 4 weeks.

On the initial day (0 week) and 4 weeks after initiation of the intake of the test food, stimulated saliva (i.e., saliva secreted from a subject chewing paraffin gum for 5 minutes) was collected from the test subjects and the number of the following bacterial cells in the oral cavity was determined: the amount of periodontal pathogens (PCR invader method); the amount of cariogenic bacteria (culture method); and the amount of lactic acid bacteria (culture method).

Furthermore, on the initial day of the intake and 4 weeks after initiation of the intake, the following items were evaluated as clinical parameters. Gingival index and bleeding on probing were evaluated by dentists.

Evaluation Items:
1) Gingival index (GI: Lee & Sillness, 1963, modified method)

Evaluation Criteria:
0: Clinically normal gum
1: Light inflammation and slight color-tone change are observed in the gum, and no bleeding is observed by rubbing the inner edge of gingival margin by a probe.
2: Medium-level inflammation, edema accompanying red flare and gloss are observed in the gum, and bleeding is observed by rubbing the inner edge of gingival margin.
3: Significant inflammation, significant red flare, and edema are observed, spontaneous bleeding occurs, and ulcer is formed.

Sites Examined:
The tongue side, lip and cheek side, mesial side, and distal side of the following 6 teeth (24 tooth surfaces in total).

TABLE 15

| Type of tooth | 6 | | 1 | 4 | |
|---|---|---|---|---|---|
| | | 4 | 1 | | 6 |

Evaluation Method

Average gingivitis score for each test subject was calculated in accordance with the following expression based on the total scores of examination sites.

$$\text{Gingivitis score} = \frac{\text{Sum of gingival indexes of individual teeth}}{\text{Number of tooth surfaces examined}}$$

2) Bleeding on probing (BOP)

Evaluation Criteria
0: No bleeding is observed
1: Bleeding is observed

Sites Examined
The tongue side, lip and cheek side, mesial side, and distal side of the following 6 teeth (24 tooth surfaces in total).

TABLE 16

| Type of tooth | 6 | | 1 | 4 | |
|---|---|---|---|---|---|
| | | 4 | 1 | | 6 |

Evaluation Method

Average bleeding score on probing for each test subject was calculated in accordance with the following expression based on the total scores of examination sites.

$$\text{Bleeding score on probing} = \frac{\text{Sum of bleeding indexes of individual teeth on probing}}{\text{Number of tooth surfaces examined}}$$

For all statistical analyses for tests in humans, statistical analysis soft (SAS preclinical package Ver. 5.0, SAS Institute Inc.) was used. In each statistical processing, the level of significance was set at 5%. Significance test was carried out between the value of week 4 or week 8 relative to the value at week 0 and change during the test period was analyzed.

The number of bacterial cells present in saliva of 17 test subjects was determined and the results are shown in Table 17. The number of the periodontal pathogens that produce bad breath-causing substances, namely, *Porphyromonas gingivalis, Fusobacterium nucleatum*, and *Tannerella forsythia* decreased at 4 weeks after initiation of intake of the lactic acid bacterium (P=0.019, 0.006, 0.005), whereas, the number of lactic acid bacillus increased at 4 weeks after initiation of intake of the lactic acid bacterium (P=0.001). No change was observed with respect to *Streptococcus mutans* during the test period.

TABLE 17

| | 0 W mean ± SD | 4 W mean ± SD | P value |
|---|---|---|---|
| *Porphyromonas gingivalis* | 4.073 ± 1.359 | 3.890 ± 1.152 | 0.019* |
| *Fusobacterium nucleatum* | 7.617 ± 0.537 | 7.240 ± 0.469 | 0.006** |
| *Tannerella forsyhia* | 6.096 ± 0.401 | 5.894 ± 0.285 | 0.005** |
| Lactic acid *bacillus* | 4.333 ± 0.770 | 5.057 ± 0.874 | 0.001** |
| *Streptococcus mutans* | 5.359 ± 0.780 | 5.596 ± 0.673 | 0.109 |

*P < 0.05,
**P < 0.01

More specifically, it was confirmed that the bacterial count of the periodontalpathogens that produces bad breath-causing substances, namely, *Porphyromonas gingivalis, Fusobacterium nucleatum*, and *Tannerella forsythia*, was decreased by intake of the lactic acid bacterium according to the present invention. From this, it was confirmed that the lactic acid bacterium is extremely useful as a prophylactic and/or therapeutic agent for oral diseases/bad breath. Furthermore, no change was observed in the bacterial count of *Streptococcus mutans*, which is a causative bacterium of caries, during the test period. Therefore, it was considered that the risk of causing caries by intake of the lactic acid bacterium according to the present invention was unlikely to become high.

Furthermore, bleeding on probing and gingival indexes were significantly low at week 4 compared to the initiation time of the intake of the lactic acid bacterium. The analysis results of the evaluation items are shown in Table 18.

TABLE 18

| | 0 W mean ± SD | 4 W mean ± SD | P value |
|---|---|---|---|
| Bleeding on probing | 0.22 ± 0.11 | 0.12 ± 0.09 | 0.008** |
| Gingival index | 1.22 ± 0.11 | 1.12 ± 0.09 | 0.008** |

*P < 0.05,
**P < 0.01

In short, an effect of the lactic acid bacterium according to the present invention in improving clinical parameters for periodontal disease such as gingivitis by intake thereof was confirmed and the lactic acid bacterium was confirmed to be extremely useful as a prophylactic and/or therapeutic agent for oral diseases/bad breath.

Test Example 11

Verification of Bad Breath Suppressive Effect in *Porphyromonas gingivalis*-positive Test Subject To investigate the effect of intake of the lactic acid bacterium, *Lactobacillus crispatus* YIT 12319, according to the present invention on bad breath, a test food containing viable bacterial cells ($3.3 \times 10^8$ cfu or more/grain) was continuously given to 7 test subjects positive for *Porphyromonas gingivalis*, which is one of the periodontal pathogens and produces bad breath-causing substances, once a day in a dose of 3 grains per time for 8 weeks. In this case, the concentration of volatile sulfur compounds (VSCs) was measured by gas chromatography.

Analysis results of VSC concentrations of a *Porphyromonas gingivalis*-positive test subject group are shown in Table 19. As a result of measuring VSC concentrations, $H_2S$ value was significantly low at 4 and 8 weeks after initiation of the lactic acid bacterium intake compared to the initiation time of the intake. In addition, the total VSC value at 8 weeks after initiation of the lactic acid bacterium intake was significantly low compared to the initiation time of the intake.

TABLE 19

| | 0 W mean ± SD | 4 W mean ± SD | P value | 8 W mean ± SD | P value |
|---|---|---|---|---|---|
| $H_2S$ | 1559.3 ± 958.2 | 835.3 ± 571.8 | 0.030* | 578.9 ± 461.9 | 0.005** |
| Total VSC | 2291.4 ± 1202.1 | 1589.9 ± 763.0 | 0.080 | 1056.1 ± 705.9 | 0.004** |

*P < 0.05,
**P < 0.01

In short, an effect of actually reducing the amount of bad breath-causing substances by intake of the lactic acid bacterium according to the present invention was confirmed and the lactic acid bacterium was confirmed to be extremely useful as a prophylactic and/or therapeutic agent for oral diseases/bad breath.

Test Example 12

Design and Synthesis of Primer

Genomic DNAs of *Lactobacillus crispatus* YIT 12319 and other 17 strains of *Lactobacillus crispatus* were compared by the RAPD method. As a result, three sites of DNA sequences specific to the target bacterial strain (*Lactobacillus crispatus* YIT 12319) were found. Subsequently, these base sequences were analyzed and primer candidates shown in Table 20 were selected. By appropriately combining these, 35 types of primer pairs specific to *Lactobacillus crispatus* YIT 12319 were designed.

TABLE 20

| Name of primer | Sequence | |
|---|---|---|
| Lc (X) 2a | gcacatcgttatagtgaacggcgc | (SEQ ID NO: 4) |
| Lc (X) 2b | cacatcgttatagtgaacggcgct | (SEQ ID NO: 5) |
| Lc (X) 2c | acggttcaatacttctaacacatccgc | (SEQ ID NO: 6) |
| Lc (X) 2d | acacatccgcttgatcttgttgttc | (SEQ ID NO: 7) |
| Lc (X) 3a | ttggttgggttaccgtcaac | (SEQ ID NO: 9) |
| Lc (X) 5a | ctttcactagtggagtgtatttac | (SEQ ID NO: 10) |
| Lc (X) 5b | gtctttcactagtggagtgtatttac | (SEQ ID NO: 11) |
| Lc (X) 5c | ctttcactagtggagtgtatttactc | (SEQ ID NO: 12) |
| Lc (X) 3b | gttgacggtaacccaaccaa | (SEQ ID NO: 13) |
| Lc (X) 5d | gtaaatacactccactagtgaaag | (SEQ ID NO: 14) |
| Lc (X) 5e | gtaaatacactccactagtgaaagac | (SEQ ID NO: 15) |
| Lc (X) 5f | gagtaaatacactccactagtgaaag | (SEQ ID NO: 16) |
| Lc (X) 6a | ttaaggtctatggaaacaactccaa | (SEQ ID NO: 17) |
| Lc (X) 7a | gtagaaaccaagttttaaggtctatg | (SEQ ID NO: 8) |

Test Example 13

Selection of Primer Pair Discriminable from the Bacteria Belonging to the Same Species of *Lactobacillus crispatus*

Figure 7:
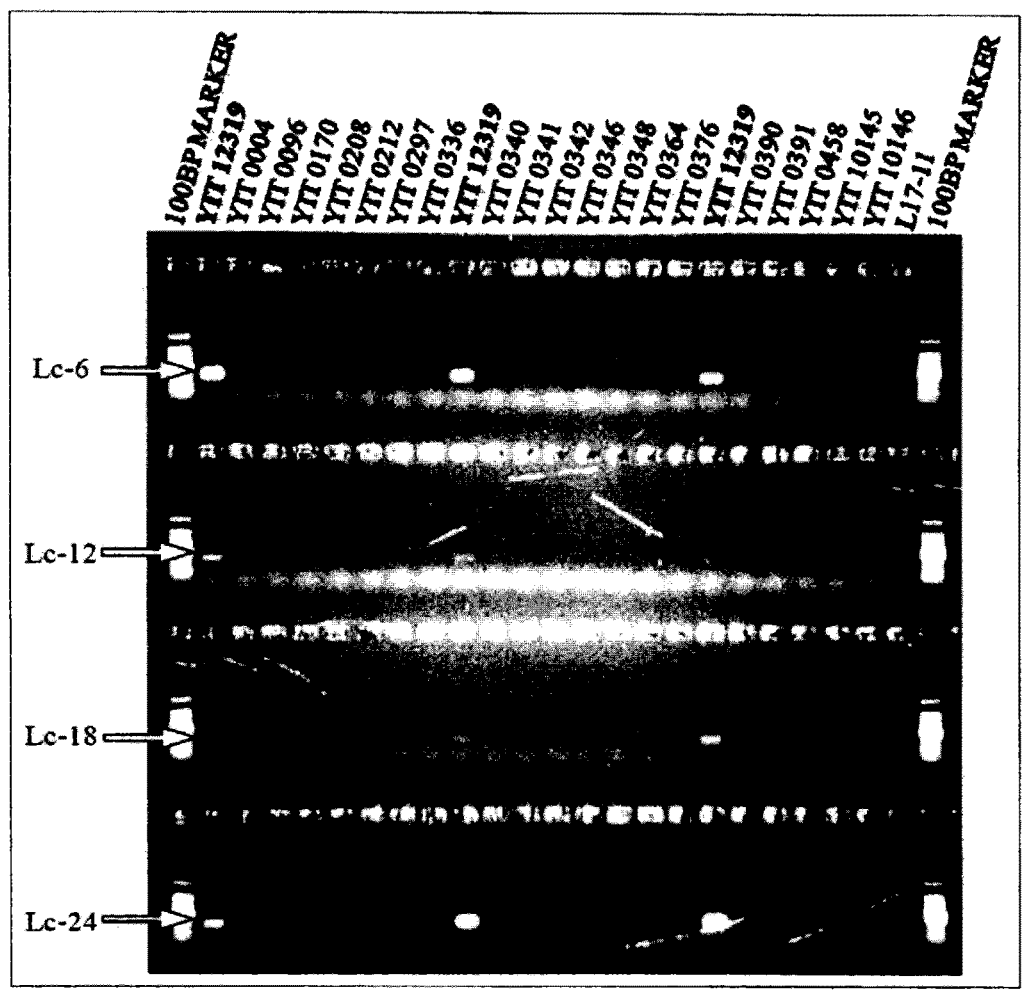
FIG. 7 is an electropherogram showing a DNA band amplified by a primer pair specific to YIT 12319 (arrows indicate specific DNA bands and the primer pairs used herein are indicated next to the corresponding arrows).

Genomic DNAs of *Lactobacillus crispatus* YIT 12319 and other 20 strains of *Lactobacillus crispatus* were subjected to PCR using 35 types of primer pairs designed. As a result, in the case where 4 types of primer pairs shown in Table 21 were used, DNA of *Lactobacillus crispatus* YIT 12319 alone was amplified by PCR (Table 21, FIG. 7).

Herein, Lc (X) 2a represents SEQ ID NO: 4; Lc (X) 2b, SEQ ID NO: 5; Lc (X) 2c, SEQ ID NO: 6; Lc (X) 2d, SEQ ID NO: 7; and Lc (X) 7a, SEQ ID NO: 8.

TABLE 21

| Name of primer pair | Primer pair | | DNA band length |
|---|---|---|---|
| | (foword) | (reverse) | (bp) |
| Lc-6 | Lc(X)2a | Lc(X)7a | 371 |
| Lc-12 | Lc(X)2b | Lc(X)7a | 370 |
| Lc-18 | Lc(X)2c | Lc(X)7a | 337 |
| Lc-24 | Lc(X)2d | Lc(X)7a | 320 |

Test Example 14

Selection of Primer Pairs Discriminable from 143 Bacterial Strains Belonging to 27 Genuses Other than *Lactobacillus crispatus*

Genomic DNAs of *Lactobacillus crispatus* YIT 12319, 65 bacterial strains of the genus *Lactobacillus* except *Lactobacillus crispatus*; 7 bacterial strains of the genus related to the genus *Lactobacillus*, and 71 bacterial strains of 22 genuses, which are predominant bacteria in an oral cavity, (27 genuses, 143 bacterial strains in total) shown in Table 22 were subjected to PCR using 4 types of primer pairs shown in Table 21. As a result, DNA of *Lactobacillus crispatus* YIT 12319 alone was amplified by PCR with any of the primer pairs tested.

In combination of the results of Test Example 13, 4 primer pairs, which do not react with 163 bacterial strains of 27 genuses and only react with *Lactobacillus crispatus* YIT 12319 were obtained.

TABLE 22

Genera and species of bacteria investigated for specificity

| Genus | Species |
|---|---|
| Actinomyces | naeslundii, viscosus, massiliensis, odontolyticus |
| Atopobium | pervulum, rimae |
| Bergeyella | zoohelcum |
| Campylobacter | concisus, gracilis |
| Capnocytophaga | gingivalis, sputigena |
| Cardiobacterium | hominis |
| Carnobacterium | maltaromaticum |
| Corynebacterium | ammoniagenes, flavescens, durum, matruchotii |
| Dorea | formicigenerans |
| Eubacterium | biforme, callanderi, cylindroides, desmolans, dolichum eligens, hadrum, hallii, rectale, siraeum |
| Fusobacterium | nucleatum, periodonticum |
| Gemella | morbillorum, haemolysans |
| Granulicatella | adiacens |
| Haemophilus | parainfuluenzae |
| Kingella | oralis |
| Lactobacillus | acetotolerans, acidophilus, agilis, almentarius, amylophilus amylovorus, animalis, aviarius, bifermentans, brevis buchneri, cacaonum, casei, catenaformis, coryniformis, crispatus curvatus, delbrueckii, equi, fabifermentans, farciminis fermentum, fructivorans, gallinarum, gasseri, graminis hamsteri, helveticus, hilgardii, homohiochii, hordei, iners intestinalis, jensenii, johnsonii, kefiranofaciens kefirgranum, kefiri, malefermentans, mali, murinus, oris panis, parabuchneri, paracollinoides, paraplantarum, pentosus plantarum, pontis, reuteri, rhamnosus, ruminis, sakei salivarius, sharpeae, sucicola, suebicus, tucceti, Vaginalis, vitulinus, zeae |
| Lautropia | mirabilis |
| Leuconostoc | fructosum |

TABLE 22-continued

Genera and species of bacteria investigated for specificity

| Genus | Species |
|---|---|
| Neiseria | mucosa, elongata, flava |
| Porphyromonas | gingivalis |
| Prevotella | denticola, intermedia, melaninogenica, oralis, oris, veroralis |
| Rothia | mucilaginosa, aeria, dentocariosa |
| Selenomonas | ruminantium |
| Slackia | exigua |
| Streptococcus | anginosus, bovis, canis, constellatus, gordonii, mitis mutans, oralis, salivarius, sanguinis, sobrinus, thermophilus |
| Veillonella | atypica, criceti, dispar, parvula, ratti |
| Weissella | confusa, halotolerans, kandleri, minor, viridescens |

Test Example 15

Production of Tablets

Components (per gain) shown in Table 23 were mixed and the mixture was formed into tablets.

TABLE 23

| Name | Formulation (g) | Proportion (%) |
|---|---|---|
| Test bacterial powder (*Lactobacillus crispatus* YIT 12319) | 0.001 ($3.3 \times 10^8$ cfu or more) | 0.14 |
| Lyophilization protecting agent (skim milk, trehalose) | 0.139 | 19.86 |
| Reduced palatinose | 0.525 | 75.00 |
| Sucrose fatty acid ester | 0.035 | 5.00 |
| Total | 0.700 | 100.00 |

The obtained tablets were stable and easy to take.

TABLE 24

| Name | Formulation (g) | Proportion (%) |
|---|---|---|
| Test bacterial powder (*Lactobacillus crispatus* YIT 12319) | 0.001 ($3.3 \times 10^8$ cfu or more) | 0.14 |
| Skim milk | 0.068 | 9.69 |
| Trehalose | 0.034 | 4.84 |
| Potato starch | 0.034 | 4.84 |
| Ascorbic acid | 0.003 | 0.484 |
| Reduced palatinose | 0.525 | 75.00 |
| Sucrose fatty acid ester | 0.035 | 5.00 |
| Total | 0.700 | 100.00 |

The obtained tablets were stable and easy to take.

The invention claimed is:

1. A method for inhibiting growth of at least one pathogenic bacterium, the method comprising administering to a subject in need thereof an effective amount of at least one lactic acid bacterium selected from the group consisting of *Lactobacillus crispatus* YIT 12319 (FERM BP-11500), *Lactobacillus fermentum* YIT 12320 (FERM BP-11501), *Lactobacillus gasseri* YIT 12321 (FERM BP-11502), and *Streptococcus mitis* YIT 12322 (FERM BP-11503),
wherein the at least one pathogenic bacterium is at least one selected from the group consisting of *Porphyromonas gingivalis, Prevotella intermedia, Aggregatibacter actinomycetemcomitans, Streptococcus mutans, Streptococcus sobrinus, Fusobacterium nucleatum*, and *Tannerella forsythia*.

2. The method of claim 1, wherein administering the at least one lactic acid bacterium comprises administering an oral composition comprising the lactic acid bacterium.

3. The method of claim 1, wherein administering the at least one lactic acid bacterium comprises administering a food or a drink comprising the lactic acid bacterium.

4. The method according to claim 3, wherein the food or the drink is a fermented product.

5. The method according to claim 1, wherein the at least one pathogenic bacterium is at least one selected from the group consisting of *Porphyromonas gingivalis, Prevotella intermedia, Aggregatibacter actinomycetemcomitans, Streptococcus mutans*, and *Streptococcus sobrinus*.

6. The method according to claim 1, wherein the at least one pathogenic bacterium is at least one selected from the group consisting of *Porphyromonas gingivalis, Fusobacterium nucleatum*, and *Tannerella forsythia*.

7. A method for preventing and/or improving bad breath, the method comprising administering to a subject in need thereof an effective amount of at least one lactic acid bacterium selected from the group consisting of *Lactobacillus crispatus YIT 12319 (FERM BP-11500), Lactobacillus fermentum YIT 12320 (FERM BP-11501), Lactobacillus gasseri YIT 12321 (FERM BP-11502), and Streptococcus mitis YIT 12322 (FERM BP-11503).

8. The method of claim 7, wherein administering the at least one lactic acid bacterium comprises administering a food or a drink comprising the lactic acid bacterium.

9. The method according to claim 8, wherein the food or the drink is a fermented product.

10. The method of claim 7, wherein administering the at least one lactic acid bacterium comprises administering an oral composition comprising the lactic acid bacterium.

11. A method for preventing and/or treating gingivitis, the method comprising administering to a subject in need thereof an effective amount of at least one lactic acid bacterium selected from the group consisting of Lactobacillus crispatus YIT 12319 (FERM BP-11500), Lactobacillus fermentum YIT 12320 (FERM BP-11501), Lactobacillus gasseri YIT 12321 (FERM BP-11502), and Streptococcus mitis YIT 12322 (FERM BP-11503).

12. The method of claim 11, wherein administering the at least one lactic acid bacterium comprises administering a food or a drink comprising the lactic acid bacterium.

13. The method according to claim 12, wherein the food or the drink is a fermented product.

14. The method of claim 11, wherein administering the at least one lactic acid bacterium comprises administering an oral composition comprising the lactic acid bacterium.

15. A method for improving bad breath, the method comprising administering to a subject in need thereof an effective amount of at least one lactic acid bacterium selected from the group consisting of Lactobacillus crispatus YIT 12319 (FERM BP-11500), Lactobacillus fermentum YIT 12320 (FERM BP-11501), Lactobacillus gasseri YIT 12321 (FERM BP-11502), and Streptococcus mitis YIT 12322 (FERM BP-11503).

16. The method of claim 15, wherein administering the at least one lactic acid bacterium comprises administering a food or a drink comprising the lactic acid bacterium.

17. The method according to claim 16, wherein the food or the drink is a fermented product.

18. The method of claim 15, wherein administering the at least one lactic acid bacterium comprises administering an oral composition comprising the lactic acid bacterium.

19. A method for treating gingivitis, the method comprising administering to a subject in need thereof an effective amount of at least one lactic acid bacterium selected from the group consisting of Lactobacillus crispatus YIT 12319 (FERM BP-11500), Lactobacillus fermentum YIT 12320 (FERM BP-11501), Lactobacillus gasseri YIT 12321 (FERM BP-11502), and Streptococcus mitis YIT 12322 (FERM BP-11503).

20. The method of claim 19, wherein administering the at least one lactic acid bacterium comprises administering a food or a drink comprising the lactic acid bacterium.

21. The method according to claim 20, wherein the food or the drink is a fermented product.

22. The method of claim 19, wherein administering the at least one lactic acid bacterium comprises administering an oral composition comprising the lactic acid bacterium.

* * * * *